(12) United States Patent
Park et al.

(10) Patent No.: US 7,001,769 B2
(45) Date of Patent: Feb. 21, 2006

(54) NUCLEIC ACID SEQUENCES AND PROTEINS INVOLVED IN CELLULAR SENESCENCE

(75) Inventors: Sang-Chul Park, Seoul (KR); Woong-Yang Park, Seoul (KR); Jeong-Soo Park, Seoul (KR); Kyung-A Cho, Seoul (KR); Deok-In Kim, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 0 days.

(21) Appl. No.: 10/363,924

(22) PCT Filed: Jul. 6, 2001

(86) PCT No.: PCT/KR01/01159

§ 371 (c)(1),
(2), (4) Date: Mar. 10, 2003

(87) PCT Pub. No.: WO02/21140

PCT Pub. Date: Mar. 14, 2002

(65) Prior Publication Data

US 2005/0261265 A1 Nov. 24, 2005

(30) Foreign Application Priority Data

Sep. 8, 2000 (KR) .......................... 2000-0053341
Sep. 8, 2000 (KR) .......................... 2000-0053342

(51) Int. Cl.
*C12N 5/02* (2006.01)
*C12P 21/06* (2006.01)

(52) U.S. Cl. ...................................... 435/377; 435/69.1
(58) Field of Classification Search .................. 514/44; 424/93.2; 536/23.1; 435/455, 69.1, 377
See application file for complete search history.

(56) References Cited

OTHER PUBLICATIONS

Deonarain. Ligand-Targeted Receptor-Mediated Vectors for Gene Delivery. Exp. Opin. Ther. Pat 1998, vol. 8. pp. 53-69.*
Gorecki, Prospects and Problems of Gene Therapy: An Update. Exp. Opin. Emerging Drugs. 2001, vol. 6(2), pp. 187-98.*
Verma, et al. Gene Therapy- Promises, Problems and Prospects. Nature. 1997, vol. 389:, pp. 239-242.*
Eck, et al. Gene-Based Therapy. In Goodman & Gilman's The Pharmacological Basis of Therapeutics, 1996, 9th Ed., McGraw-Hill, New York, NY., pp. 77-101.*
David et al. Autoimmunity in Stiff-Man Syndrome with Breast Cancer is Targetedd to the C-Terminal Region of Human Amphiphysin, a Protein Similar to the Yeast Proteins, Rvs167 and Rvs 161. FEBS Letters, 1994, vol. 351, pp. 73-79.*
W.-Y.- Park et al; "Up-regulation of Caveolin Attenuates Epidermal Growth Factor Signaling in Senescent Cells", J. Biol. Chem., vol. 275 (27), Jul. 7, 2000 pp. 20847-20852.

* cited by examiner

*Primary Examiner*—Deborah Crouch
(74) *Attorney, Agent, or Firm*—Nixon & Vanderhye P.C.

(57) ABSTRACT

The present invention relates to nucleic acid sequences and proteins involved in senescence and particularly, to nucleic acid sequences and proteins including amphiphysin and caveolin involved in cellular senescence and their use.

3 Claims, 16 Drawing Sheets

A pcDNA3   pCav-1

Cav-1

B

| | pcDNA3 | | | pCav-1 | | | |
|---|---|---|---|---|---|---|---|
| EGF | 0 | 5 | 20 | 0 | 5 | 20 | min | p-Erk-1/2

Erk-1/2

−  +

SEQUENCE LISTING

```
<160> NUMBER OF SEQ ID NOS: 10

<210> SEQ ID NO 1
<211> LENGTH: 2377
<212> TYPE: DNA
<213> ORGANISM: Homo sapiens
<220> FEATURE:
<221> NAME/KEY: CDS
<222> LOCATION: (111)..(2195)
<223> OTHER INFORMATION: amphiphysin-1 cDNA

<400> SEQUENCE: 1
cggctctcag ctgcactcct gtacatccac ctgtcttcag gagagcactg tttgtgtgtg      60
cccagccccg ctgcgcgctc tgctcttcgc agctcccgg acccgcagcc atg gcc gac     119
                                                      Met Ala Asp
                                                        1 atc aag acg ggc atc ttc gcc aag aac atc cag aag cga ctc aac cgc      167
Ile Lys Thr Gly Ile Phe Ala Lys Asn Ile Gln Lys Arg Leu Asn Arg
  5                  10                  15
```

-continued

| | | |
|---|---|---|
| gcg cag gaa aag gtc ctc caa aag ctg ggg aaa gct gat gag aca aaa<br>Ala Gln Glu Lys Val Leu Gln Lys Leu Gly Lys Ala Asp Glu Thr Lys<br>20                     25                     30                    35 | | 215 |
| gac gaa cag ttc gaa gaa tat gtc cag aac ttc aaa cgg caa gaa gca<br>Asp Glu Gln Phe Glu Glu Tyr Val Gln Asn Phe Lys Arg Gln Glu Ala<br>                      40                     45                     50 | | 263 |
| gag ggt acc aga ctt cag cga gaa ctc cga gga tat tta gca gca atc<br>Glu Gly Thr Arg Leu Gln Arg Glu Leu Arg Gly Tyr Leu Ala Ala Ile<br>                55                     60                     65 | | 311 |
| aaa ggc atg cag gag gcc tcc atg aag ctc aca gag tcg ctg cat gaa<br>Lys Gly Met Gln Glu Ala Ser Met Lys Leu Thr Glu Ser Leu His Glu<br>        70                     75                     80 | | 359 |
| gtc tat gag cct gac tgg tat ggg cgg gaa gat gtg aaa atg gtt ggt<br>Val Tyr Glu Pro Asp Trp Tyr Gly Arg Glu Asp Val Lys Met Val Gly<br>      85                     90                     95 | | 407 |
| gag aaa tgt gat gtg ctg tgg gaa gac ttc cat caa aaa ctc gtg gat<br>Glu Lys Cys Asp Val Leu Trp Glu Asp Phe His Gln Lys Leu Val Asp<br>100                     105                  110               115 | | 455 |
| ggg tcc ttg cta aca ctg gat acc tac ctg ggg caa ttt cct gac ata<br>Gly Ser Leu Leu Thr Leu Asp Thr Tyr Leu Gly Gln Phe Pro Asp Ile<br>                120                  125               130 | | 503 |
| aag aat cgc atc gcc aag cgc agc agg aag cta gtg gac tat gac agt<br>Lys Asn Arg Ile Ala Lys Arg Ser Arg Lys Leu Val Asp Tyr Asp Ser<br>           135                  140               145 | | 551 |
| gcc cgc cac cat ctg gaa gct ctg cag agc tcc aag agg aag gat gag<br>Ala Arg His His Leu Glu Ala Leu Gln Ser Ser Lys Arg Lys Asp Glu<br>150                     155                  160 | | 599 |
| agt cga atc tct aag gca gaa gaa gaa ttt cag aaa gca cag aaa gtg<br>Ser Arg Ile Ser Lys Ala Glu Glu Glu Phe Gln Lys Ala Gln Lys Val<br>           165                  170               175 | | 647 |
| ttt gaa gag ttt aac gtt gac tta caa gaa gag tta cca tca tta tgg<br>Phe Glu Glu Phe Asn Val Asp Leu Gln Glu Glu Leu Pro Ser Leu Trp<br>180                     185                  190               195 | | 695 |
| tca aga cga gtt gga ttt tat gtt aat act ttc aaa aac gtc tcc agc<br>Ser Arg Arg Val Gly Phe Tyr Val Asn Thr Phe Lys Asn Val Ser Ser<br>                200                  205               210 | | 743 |
| ctt gaa gcc aag ttt cat aag gaa att gcg gtg ctt tgc cac aaa ctg<br>Leu Glu Ala Lys Phe His Lys Glu Ile Ala Val Leu Cys His Lys Leu<br>           215                  220               225 | | 791 |
| tat gaa gtg atg aca aaa ctg ggt gac cag cac gcc gac aag gcc ttc<br>Tyr Glu Val Met Thr Lys Leu Gly Asp Gln His Ala Asp Lys Ala Phe<br>230                     235                  240 | | 839 |
| acc atc caa gga gcg ccc agt gat tcg ggt cct ctc cgc att gca aag<br>Thr Ile Gln Gly Ala Pro Ser Asp Ser Gly Pro Leu Arg Ile Ala Lys<br>245                     250                  255 | | 887 |
| aca cca tca ccg cct gag gag cct tca ccc ctc ccg agc ccg aca gca<br>Thr Pro Ser Pro Pro Glu Glu Pro Ser Pro Leu Pro Ser Pro Thr Ala<br>260                     265                  270               275 | | 935 |
| agt cca aat cat aca tta gca cct gcg tct ccc gca cca gca cgg cct<br>Ser Pro Asn His Thr Leu Ala Pro Ala Ser Pro Ala Pro Ala Arg Pro<br>                280                  285               290 | | 983 |
| cgg tca cct tca cag aca agg aaa ggg cct cct gtc cca cct cta cct<br>Arg Ser Pro Ser Gln Thr Arg Lys Gly Pro Pro Val Pro Pro Leu Pro<br>           295                  300               305 | | 1031 |
| aaa gtc acc ccg aca aag gaa ctg cag cag gag aac atc atc agt ttc<br>Lys Val Thr Pro Thr Lys Glu Leu Gln Gln Glu Asn Ile Ile Ser Phe<br>310                     315                  320 | | 1079 |
| ttt gag gac aac ttt gtt cca gaa atc agt gtg aca aca cct tcc cag<br>Phe Glu Asp Asn Phe Val Pro Glu Ile Ser Val Thr Thr Pro Ser Gln<br>325                     330                  335 | | 1127 |

| | |
|---|---|
| aat gaa gtc cct gag gtg aag aaa gag gag act ttg ctg gat ctg gac<br>Asn Glu Val Pro Glu Val Lys Lys Glu Glu Thr Leu Leu Asp Leu Asp<br>340                       345                   350                     355 | 1175 |
| ttt gat cct ttc aag ccc gag gtg aca cct gca ggt tct gct gga gtg<br>Phe Asp Pro Phe Lys Pro Glu Val Thr Pro Ala Gly Ser Ala Gly Val<br>                   360                   365                     370 | 1223 |
| acc cac tca ccc atg tct cag aca ttg ccc tgg gac cta tgg acg aca<br>Thr His Ser Pro Met Ser Gln Thr Leu Pro Trp Asp Leu Trp Thr Thr<br>                375                   380                   385 | 1271 |
| agc act gat ttg gta cag ccg gct tct ggt ggt tca ttt aat gga ttc<br>Ser Thr Asp Leu Val Gln Pro Ala Ser Gly Gly Ser Phe Asn Gly Phe<br>          390                   395                   400 | 1319 |
| aca cag ccc cag gat act tca tta ttc aca atg cag aca gac cag agt<br>Thr Gln Pro Gln Asp Thr Ser Leu Phe Thr Met Gln Thr Asp Gln Ser<br>405                       410                   415 | 1367 |
| atg atc tgc aac ttg gct gaa tct gaa cag gct cca ccc aca gag cca<br>Met Ile Cys Asn Leu Ala Glu Ser Glu Gln Ala Pro Pro Thr Glu Pro<br>420                       425                   430                     435 | 1415 |
| aaa gca gag gag cct ctg gct gct gtc aca cct gcc gtt ggt ctg gac<br>Lys Ala Glu Glu Pro Leu Ala Ala Val Thr Pro Ala Val Gly Leu Asp<br>                   440                   445                     450 | 1463 |
| ctt gga atg gac act cgg gct gag gag cca gtg gag gag gca gtg atc<br>Leu Gly Met Asp Thr Arg Ala Glu Glu Pro Val Glu Glu Ala Val Ile<br>                455                   460                   465 | 1511 |
| ata cct gga gct gat gct gat gca gct gtt gga acc ttg gtg tca gca<br>Ile Pro Gly Ala Asp Ala Asp Ala Ala Val Gly Thr Leu Val Ser Ala<br>          470                   475                   480 | 1559 |
| gct gag ggg gcc cca gga gag gaa gca gag gcg gag aag gcc act gtc<br>Ala Glu Gly Ala Pro Gly Glu Glu Ala Glu Ala Glu Lys Ala Thr Val<br>485                       490                   495 | 1607 |
| cct gcc ggg gaa gga gta agt tta gag gag gcc aaa att gga act gaa<br>Pro Ala Gly Glu Gly Val Ser Leu Glu Glu Ala Lys Ile Gly Thr Glu<br>500                       505                   510                     515 | 1655 |
| acc act gag ggt gca gag agt gcc caa cct gaa gca gag gag ctc gaa<br>Thr Thr Glu Gly Ala Glu Ser Ala Gln Pro Glu Ala Glu Glu Leu Glu<br>                   520                   525                     530 | 1703 |
| gca aca gtg cct cag gag aag gtc att cct tcg gtg gtc ata gag cct<br>Ala Thr Val Pro Gln Glu Lys Val Ile Pro Ser Val Val Ile Glu Pro<br>                535                   540                   545 | 1751 |
| gcc tcc aac cat gaa gag gaa gga gaa aac gaa ata act ata ggt gca<br>Ala Ser Asn His Glu Glu Glu Gly Glu Asn Glu Ile Thr Ile Gly Ala<br>          550                   555                   560 | 1799 |
| gag ccc aag gag acc acc gag gac gcg gct cct ccg ggc ccc acc agc<br>Glu Pro Lys Glu Thr Thr Glu Asp Ala Ala Pro Pro Gly Pro Thr Ser<br>565                       570                   575 | 1847 |
| gag aca ccg gag ctg gct acg gag cag aag cct atc cag gac cct cag<br>Glu Thr Pro Glu Leu Ala Thr Glu Gln Lys Pro Ile Gln Asp Pro Gln<br>580                       585                   590                     595 | 1895 |
| ccc acg cct tct gca cca gcc atg ggg gct gct gac cag cta gca tct<br>Pro Thr Pro Ser Ala Pro Ala Met Gly Ala Ala Asp Gln Leu Ala Ser<br>                   600                   605                   610 | 1943 |
| gca agg gag gcc tct cag gaa ttg cct cct ggc ttt ctc tac aag gtg<br>Ala Arg Glu Ala Ser Gln Glu Leu Pro Pro Gly Phe Leu Tyr Lys Val<br>                615                   620                   625 | 1991 |
| gaa aca ctg cat gat ttt gag gca gca aat tct gat gaa ctt acc tta<br>Glu Thr Leu His Asp Phe Glu Ala Ala Asn Ser Asp Glu Leu Thr Leu<br>          630                   635                   640 | 2039 |
| caa agg ggt gat gtg gtg ctg gtg gtc ccc tca gat tca gaa gct gat<br>Gln Arg Gly Asp Val Val Leu Val Val Pro Ser Asp Ser Glu Ala Asp | 2087 |

```
                645                 650                 655
cag gat gca ggc tgg ctg gtg gga gtg aag gaa tca gac tgg ctt cag    2135
Gln Asp Ala Gly Trp Leu Val Gly Val Lys Glu Ser Asp Trp Leu Gln
660                 665                 670                 675 tac aga gac ctt gcc acc tac aaa ggc ctc ttt cca gag aac ttc acc    2183
Tyr Arg Asp Leu Ala Thr Tyr Lys Gly Leu Phe Pro Glu Asn Phe Thr
                680                 685                 690 cga cgc tta gat taggg caacaagtac tgcaagaagg agctcagtta cggggttttt  2240
Arg Arg Leu Asp
            695 aaaccttcat gaaacctga agagttcact tttgttatta tgctcttaat gatttacaga   2300 ctgatgccag acaaaccttg ggaagatgta tcaatggagc atgtgtgcaa aaaaatgtaa  2360 gaggaaaaaa aaaaccg                                                 2377

<210> SEQ ID NO 2
<211> LENGTH: 695
<212> TYPE: PRT
<213> ORGANISM: Homo sapiens

<400> SEQUENCE: 2

Met Ala Asp Ile Lys Thr Gly Ile Phe Ala Lys Asn Ile Gln Lys Arg
1               5                   10                  15

Leu Asn Arg Ala Gln Glu Lys Val Leu Gln Lys Leu Gly Lys Ala Asp
            20                  25                  30

Glu Thr Lys Asp Glu Gln Phe Glu Glu Tyr Val Gln Asn Phe Lys Arg
        35                  40                  45

Gln Glu Ala Glu Gly Thr Arg Leu Gln Arg Glu Leu Arg Gly Tyr Leu
    50                  55                  60

Ala Ala Ile Lys Gly Met Gln Glu Ala Ser Met Lys Leu Thr Glu Ser
65                  70                  75                  80

Leu His Glu Val Tyr Glu Pro Asp Trp Tyr Gly Arg Glu Asp Val Lys
                85                  90                  95

Met Val Gly Glu Lys Cys Asp Val Leu Trp Glu Asp Phe His Gln Lys
            100                 105                 110

Leu Val Asp Gly Ser Leu Leu Thr Leu Asp Thr Tyr Leu Gly Gln Phe
        115                 120                 125

Pro Asp Ile Lys Asn Arg Ile Ala Lys Arg Ser Arg Lys Leu Val Asp
    130                 135                 140

Tyr Asp Ser Ala Arg His His Leu Glu Ala Leu Gln Ser Ser Lys Arg
145                 150                 155                 160

Lys Asp Glu Ser Arg Ile Ser Lys Ala Glu Glu Phe Gln Lys Ala
                165                 170                 175

Gln Lys Val Phe Glu Glu Phe Asn Val Asp Leu Gln Glu Glu Leu Pro
            180                 185                 190

Ser Leu Trp Ser Arg Arg Val Gly Phe Tyr Val Asn Thr Phe Lys Asn
        195                 200                 205

Val Ser Ser Leu Glu Ala Lys Phe His Lys Glu Ile Ala Val Leu Cys
    210                 215                 220

His Lys Leu Tyr Glu Val Met Thr Lys Leu Gly Asp Gln His Ala Asp
225                 230                 235                 240

Lys Ala Phe Thr Ile Gln Gly Ala Pro Ser Asp Ser Gly Pro Leu Arg
                245                 250                 255

Ile Ala Lys Thr Pro Ser Pro Pro Glu Glu Pro Ser Pro Leu Pro Ser
            260                 265                 270
```

```
Pro Thr Ala Ser Pro Asn His Thr Leu Ala Pro Ala Ser Pro Ala Pro
        275                 280                 285

Ala Arg Pro Arg Ser Pro Ser Gln Thr Arg Lys Gly Pro Pro Val Pro
        290                 295                 300

Pro Leu Pro Lys Val Thr Pro Thr Lys Glu Leu Gln Gln Glu Asn Ile
305                 310                 315                 320

Ile Ser Phe Phe Glu Asp Asn Phe Val Pro Glu Ile Ser Val Thr Thr
                325                 330                 335

Pro Ser Gln Asn Glu Val Pro Glu Val Lys Lys Glu Glu Thr Leu Leu
            340                 345                 350

Asp Leu Asp Phe Asp Pro Phe Lys Pro Glu Val Thr Pro Ala Gly Ser
        355                 360                 365

Ala Gly Val Thr His Ser Pro Met Ser Gln Thr Leu Pro Trp Asp Leu
    370                 375                 380

Trp Thr Thr Ser Thr Asp Leu Val Gln Pro Ala Ser Gly Gly Ser Phe
385                 390                 395                 400

Asn Gly Phe Thr Gln Pro Gln Asp Thr Ser Leu Phe Thr Met Gln Thr
                405                 410                 415

Asp Gln Ser Met Ile Cys Asn Leu Ala Glu Ser Glu Gln Ala Pro Pro
            420                 425                 430

Thr Glu Pro Lys Ala Glu Pro Leu Ala Ala Val Thr Pro Ala Val
        435                 440                 445

Gly Leu Asp Leu Gly Met Asp Thr Arg Ala Glu Pro Val Glu Glu
    450                 455                 460

Ala Val Ile Ile Pro Gly Ala Asp Ala Asp Ala Ala Val Gly Thr Leu
465                 470                 475                 480

Val Ser Ala Ala Glu Gly Ala Pro Gly Glu Glu Ala Glu Ala Glu Lys
                485                 490                 495

Ala Thr Val Pro Ala Gly Glu Gly Val Ser Leu Glu Glu Ala Lys Ile
            500                 505                 510

Gly Thr Glu Thr Thr Glu Gly Ala Glu Ser Ala Gln Pro Glu Ala Glu
        515                 520                 525

Glu Leu Glu Ala Thr Val Pro Gln Glu Lys Val Ile Pro Ser Val Val
    530                 535                 540

Ile Glu Pro Ala Ser Asn His Glu Glu Glu Gly Glu Asn Glu Ile Thr
545                 550                 555                 560

Ile Gly Ala Glu Pro Lys Glu Thr Thr Glu Asp Ala Ala Pro Pro Gly
                565                 570                 575

Pro Thr Ser Glu Thr Pro Glu Leu Ala Thr Glu Gln Lys Pro Ile Gln
            580                 585                 590

Asp Pro Gln Pro Thr Pro Ser Ala Pro Ala Met Gly Ala Ala Asp Gln
        595                 600                 605

Leu Ala Ser Ala Arg Glu Ala Ser Gln Glu Leu Pro Pro Gly Phe Leu
    610                 615                 620

Tyr Lys Val Glu Thr Leu His Asp Phe Glu Ala Ala Asn Ser Asp Glu
625                 630                 635                 640

Leu Thr Leu Gln Arg Gly Asp Val Val Leu Val Val Pro Ser Asp Ser
                645                 650                 655

Glu Ala Asp Gln Asp Ala Gly Trp Leu Val Gly Val Lys Glu Ser Asp
            660                 665                 670

Trp Leu Gln Tyr Arg Asp Leu Ala Thr Tyr Lys Gly Leu Phe Pro Glu
        675                 680                 685

Asn Phe Thr Arg Arg Leu Asp
```

```
<210> SEQ ID NO 3
<211> LENGTH: 829
<212> TYPE: DNA
<213> ORGANISM: Homo sapiens
<220> FEATURE:
<221> NAME/KEY: CDS
<222> LOCATION: (26)..(559)
<223> OTHER INFORMATION: caveolin-1 cDNA

<400> SEQUENCE: 3
```

| | | |
|---|---|---|
| agttttcatc cagccacggg ccagc atg tct ggg ggc aaa tac gta gac | | 49 |
| Met Ser Gly Gly Lys Tyr Val Asp | | |
| 1 5 | | |
| tcg gag gga cat ctc tac acc gtt ccc atc cgg gaa cag ggc aac atc | | 97 |
| Ser Glu Gly His Leu Tyr Thr Val Pro Ile Arg Glu Gln Gly Asn Ile | | |
| 10 15 20 | | |
| tac aag ccc aac aac aag gcc atg gca gac gag ctg agc gag aag caa | | 145 |
| Tyr Lys Pro Asn Asn Lys Ala Met Ala Asp Glu Leu Ser Glu Lys Gln | | |
| 25 30 35 40 | | |
| gtg tac gac gcg cac acc aag gag atc gac ctg gtc aac cgc gac cct | | 193 |
| Val Tyr Asp Ala His Thr Lys Glu Ile Asp Leu Val Asn Arg Asp Pro | | |
| 45 50 55 | | |
| aaa cac ctc aac gat gac gtg gtc aag att gac ttt gaa gat gtg att | | 241 |
| Lys His Leu Asn Asp Asp Val Val Lys Ile Asp Phe Glu Asp Val Ile | | |
| 60 65 70 | | |
| gca gaa cca gaa ggg aca cac agt ttt cac ggc att tgg aag gcc agc | | 289 |
| Ala Glu Pro Glu Gly Thr His Ser Phe His Gly Ile Trp Lys Ala Ser | | |
| 75 80 85 | | |
| ttc acc acc ttc act gtg acg aaa tac tgg ttt tac cgc ttg ctg tct | | 337 |
| Phe Thr Thr Phe Thr Val Thr Lys Tyr Trp Phe Tyr Arg Leu Leu Ser | | |
| 90 95 100 | | |
| gcc ctc ttt ggc atc ccg atg gca ctc atc tgg ggc att tac ttc gcc | | 385 |
| Ala Leu Phe Gly Ile Pro Met Ala Leu Ile Trp Gly Ile Tyr Phe Ala | | |
| 105 110 115 120 | | |
| att ctc tct ttc ctg cac atc tgg gca gtt gta cca tgc att aag agc | | 433 |
| Ile Leu Ser Phe Leu His Ile Trp Ala Val Val Pro Cys Ile Lys Ser | | |
| 125 130 135 | | |
| ttc ctg att gag att cag tgc acc agc cgt gtc tat tcc atc tac gtc | | 481 |
| Phe Leu Ile Glu Ile Gln Cys Thr Ser Arg Val Tyr Ser Ile Tyr Val | | |
| 140 145 150 | | |
| cac acc gtc tgt gac cca ctc ttt gaa gct gtt ggg aaa ata ttc agc | | 529 |
| His Thr Val Cys Asp Pro Leu Phe Glu Ala Val Gly Lys Ile Phe Ser | | |
| 155 160 165 | | |
| aat gtc cgc atc aac ttg cag aaa gaa ata t aaatgacatt tcaaggatag | | 580 |
| Asn Val Arg Ile Asn Leu Gln Lys Glu Ile | | |
| 170 175 | | |
| aagtatacct gatttttttt ccttttaatt ttcctggtgc caatttcaag ttccaagttg | | 640 |
| ctaatacagc aacgaattta tgaattgaat tatcttggtt gaaataaaaa agatcacttt | | 700 |
| ctcagttttc ataagtatta tgtctcttct gagctatttc atctattttt ggcagtctga | | 760 |
| atttttaaaa cccatttata tttctttcct tacctttttta tttgcatgtg gatcaaccat | | 820 |
| cgctttatt | | 829 |

```
<210> SEQ ID NO 4
<211> LENGTH: 178
<212> TYPE: PRT
<213> ORGANISM: Homo sapiens

<400> SEQUENCE: 4
```

```
Met Ser Gly Gly Lys Tyr Val Asp Ser Glu Gly His Leu Tyr Thr Val
 1               5                  10                  15

Pro Ile Arg Glu Gln Gly Asn Ile Tyr Lys Pro Asn Asn Lys Ala Met
            20                  25                  30

Ala Asp Glu Leu Ser Glu Lys Gln Val Tyr Asp Ala His Thr Lys Glu
        35                  40                  45

Ile Asp Leu Val Asn Arg Asp Pro Lys His Leu Asn Asp Val Val
    50                  55                  60

Lys Ile Asp Phe Glu Asp Val Ile Ala Glu Pro Glu Gly Thr His Ser
 65              70                  75                  80

Phe His Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
            115                 120                 125

Ala Val Val Pro Cys Ile Lys Ser Phe Leu Ile Glu Ile Gln Cys Thr
        130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence:
      amphiphysin-1 primer

<400> SEQUENCE: 5
aactgtccac catggccgac atcaagacgg gc                                32

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      amphiphysin-1 primer

<400> SEQUENCE: 6
ggatccctaa tctaagcgtc gggt                                        24

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence:forward
      primer

<400> SEQUENCE: 7
aactgtccac catgagtgat cgggtcctc tccgc                             35

<210> SEQ ID NO 8
<211> LENGTH: 30
<212> TYPE: DNA
```

```
<213> ORGANISM: Artificial Sequence
<220> FEATURE:
<223> OTHER INFORMATION: Description of Artificial Sequence:reverse
      primer

<400> SEQUENCE: 8
ggatccctac tgctccgtag ccagctccgg                                           30

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence:forward
      primer

<400> SEQUENCE: 9
atccaagctt ccaccatgtc tgggggcaaa tacgt                                     35

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:reverse
      primer

<400> SEQUENCE: 10
gcaggatccc tatatttctt tctgcaagtt gat                                       33
```

US 7,001,769 B2

NUCLEIC ACID SEQUENCES AND PROTEINS INVOLVED IN CELLULAR SENESCENCE

The present application is a 371 U.S. National Phase of International Application PCT/KR01/01159, filed Jul. 6, 2001, which designated the U.S.

BACKGROUND OF THE INVENTION

1. Field of the Invention

The present invention relates to nucleic acid sequences and proteins involved in senescence and particularly, to nucleic acid sequences and proteins involved in cellular senescence and their use.

2. Description of the Related Art

The mechanism on senescence (also, called "aging") was intensively studied and a variety of hypotheses were suggested. The hypothesis comprises (a) free radical theory of aging (Harman D, Proc. Natl. Acad. Sci., 78, 7124–7128 (1981)), (b) crosslinking theory of aging (Bjorksten J., *J. Am. Geriatr Soc.*, 16, 408–423 (1968)), (c) mitochondrial theory of aging (Lee C M et al., *Free Radic. Biol. Med.*, 22, 1259–1269 (1997); and Wallace D C et al., *Biofactors*, 7, 187–190 (1998)), and (d) genetic program theory of aging (Harley C B et al., *Curr. Opin. Genet. Dev.*, 5, 249–255 (1995)).

Moreover, the senescence has been investigated in cellular level, i.e., cellular senescence. According to the investigation, senescent cell is characterized by (a) arrest of cell cycle at G1 phase, (b) diminished physiological functions (Goldstein, *Science*, 249:1129–1133 (1990); Campisi J., *Cell*, 84:497–500 (1996)), and (c) resistance to apoptotic-programmed-cell death (Wang E., *Cancer Res.*, 55:2284–2292 (1995)).

A large variety of studies on cellular senescence have been made with human fibroblasts since the cells are considered to reflect a senescence phenomenon in individual level (Campisi J., *Cell*, 84:497–500(1996)).

Meanwhile, the patent applications related to nucleic acid and proteins associated with aging process, disclosed in WO 99/52929 and WO 01/23615.

As described above, a variety of theories have been proposed, there remains a need of more evident elucidation for cellular senescence, a need of specific biomarker for identifying senescent cell, and a need of biomolecule for modulating cellular senescence.

In particular, the prospect of reversing senescence and restoring normal physiological function has an importance in certain diseases associated with senescence, for example, Werner Syndrome and Hutchinson-Gilford Syndrome.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

In one aspect of this invention, there is provided a method for detecting a senescent cell comprising determining the amount of a protein involved in cellular senescence of a cell, wherein the protein is one or more selected from the group consisting of amphiphysin protein and caveolin protein.

In another aspect of this invention, there is provided a method for detecting a senescent cell comprising determining the amount of a polynucleotide encoding a protein involved in cellular senescence of a cell, wherein the protein is one or more selected from the group consisting of amphiphysin protein and caveolin protein.

In still another aspect of this invention, there is provided a composition for modulating cellular senescence comprising the effective amount of a protein involved in cellular senescence, wherein the protein is selected from the group consisting of amphiphysin protein and caveolin protein.

In further aspect of this invention, there is provided a composition for modulating cellular senescence comprising the effective amount of a polynucleotide encoding a protein involved in cellular senescence, wherein the protein is selected from the group consisting of amphiphysin protein and caveolin protein.

In still further aspect of this invention, there is provided a composition for modulating cellular senescence comprising the effective amount of an antisense oligonucleotide which hybridizes to a polynucleotide encoding a protein involved in cellular senescence and thereby inhibits the polynucleotide from expressing the protein, wherein the protein is selected from the group consisting of amphiphysin protein and caveolin protein.

In another aspect of this invention, there is provided a composition for modulating cellular senescence comprising the effective amount of a methylating agent or a demethylating agent, in which the agent methylates or demethylates bases of a polynucleotide encoding caveolin protein.

In still another aspect of this invention, there is provided a composition for modulating cellular senescence comprising the effective amount of dominant negative amphiphysin-1 gene.

In further aspect of this invention, there is provided a method for modulating cellular senescence in a patient in need thereof, comprising administering to the patient the effective amount of a protein involved in cellular senescence, wherein the protein is selected from the group consisting of amphiphysin protein and caveolin protein.

In still further aspect of this invention, there is provided a method for modulating cellular senescence in a patient in need thereof, comprising administering to the patient the effective amount of a polynucleotide encoding a protein involved in cellular senescence, wherein the protein is selected from the group consisting of amphiphysin protein and caveolin protein.

In another aspect of this invention, there is provided a method for modulating cellular senescence in a patient in need thereof, comprising administering to the patient the effective amount of an antisense oligonucleotide which hybridizes to a polynucleotide encoding a protein involved in cellular senescence and thereby inhibits the polynucleotide from expressing the protein, wherein the protein is selected from the group consisting of amphiphysin protein and caveolin protein.

In still another aspect of this invention, there is provided a method for modulating cellular senescence in a patient in need thereof, comprising administering to the patient the effective amount of a methylating agent or a demethylating agent, in which the agent methylates or demethylates bases of a polynucleotide encoding caveolin protein.

In further aspect of this invention, there is provided a method for identifying a substance affecting the senescence of a cell, which comprises: (a) culturing the cell in the presence of the substance to be tested; (b) isolating a protein from the cell; (c) contacting the isolated protein with an antibody specific to a protein involved in cellular senescence, wherein the protein is selected from the group consisting of amphiphysin protein and caveolin protein; and (d) determining the amount of the isolated protein bound to the antibody.

In still further aspect of this invention, there is provided a method for identifying a substance affecting the senescence of a cell, which comprises: (a) culturing the cell in the presence of the substance to be tested; (b) isolating RNA from the cell; (c) contacting the isolated RNA with a polynucleotide encoding a protein involved in cellular senescence, wherein the protein is selected from the group consisting of amphiphysin protein and caveolin protein; and (d) determining the amount of the isolated RNA hybridized to the polynucleotide encoding a protein involved in endocytosis.

In another aspect of this invention, there is provided a kit for detecting a senescent cell comprising a probe derived from a polynucleotide encoding a protein involved in cellular senescence, wherein the protein is selected from the group consisting of amphiphysin protein and caveolin protein.

In still another aspect of this invention, there is provided a biomarker for identifying cellular senescence comprising a protein involved in cellular senescence, wherein the protein is selected from the group consisting of amphiphysin protein and caveolin protein.

In further aspect of this invention, there is provided a biomarker for identifying cellular senescence comprising a polynucleotide encoding a protein involved in cellular senescence, wherein the protein is selected from the group consisting of amphiphysin protein and caveolin protein.

Accordingly, it is an object of this invention to provide a method for detecting a senescent cell.

It is another object of this invention to provide a composition for modulating cellular senescence.

It is still another object of this invention to provide a method for modulating cellular senescence in a patient in need thereof.

It is further object of this invention to provide a method for identifying a substance affecting the senescence of a cell.

It is still further object of this invention to provide a kit for detecting a senescent cell. It is another object of this invention to provide a biomarker for identifying cellular senescence.

Other objects and advantages of the present invention will become apparent from the detailed description to follow taken in conjugation with the appended claims and drawings.

DETAILED DESCRIPTION OF THIS INVENTION

Figure 1:
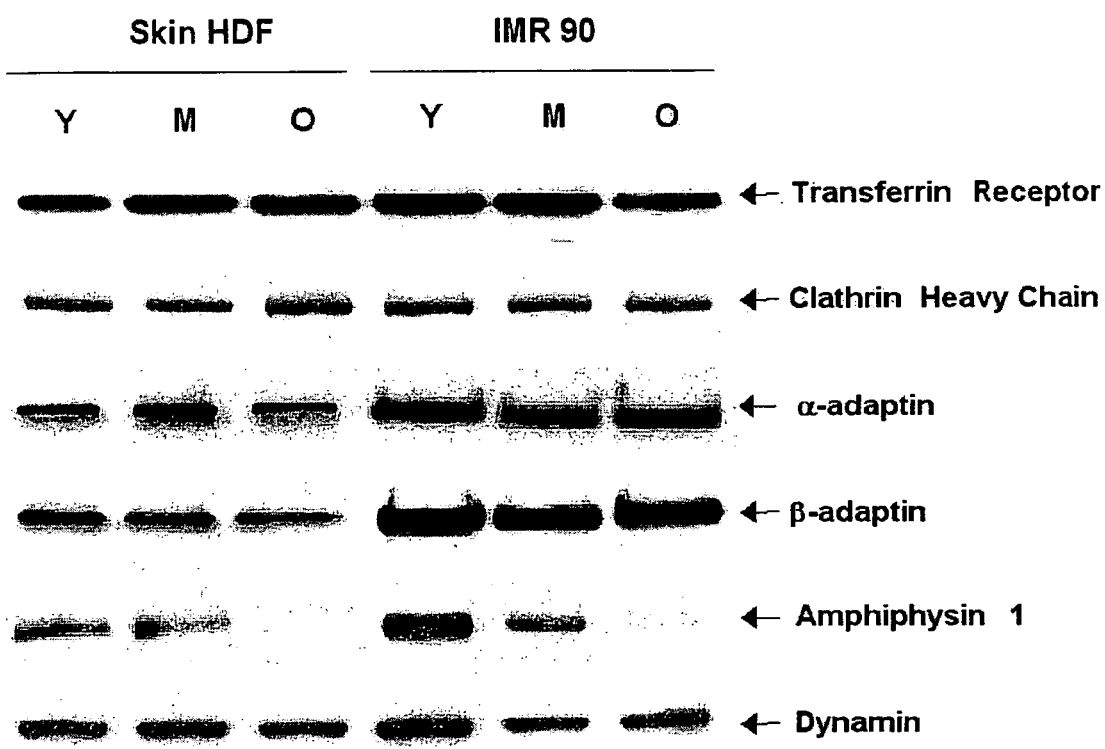
FIG. 1 is a photograph showing the results of western blotting for analyzing the expression of proteins associated with cellular senescence.

The present invention, in principle, is directed to nucleic acids and proteins modulating cellular senescence. The inventors have found that amphiphysin and caveolin are responsible for cell senescence in each different manner, as demonstrated in Example.

The process of receptor-mediated endocytosis via clathrin-coated vesicle is composed of several steps, which include recruitment of the clathrin coats and fission of the coated bud (Schmid, S. L. *Annu. Rev. Biochem.,* 66:511–548 (1997)). After binding of ligand to the receptor, such as epidermal growth factor (hereinafter referred at as "EGF"), receptor tyrosine kinase phophorylates clathrin, which in turn can provide a binding site for Src-homology-3 (SH3) domain of amphiphysin (Slepnev, V. I. et al., Science, 281:821–824 (1998); Wang, L. H. et al., *J. Biol. Chem.,* 270:10079–10083 (1995); and Ramjaun, A. R. et al., J.

Neurochem., 70:2369–2376 (1998)). Although its precise mechanism of action is not clear, amphiphysin-1 is thought to involve the recruitment and oligomerization at the neck of endocytotic buds (Schmid, S. L. *Annu. Rev. Biochem.*, 66:511–548 (1997); and Takei, K. et al., *Nat. Cell Biol.*, 133–139 (1999)). Amphiphysin-1 bridges the AP2/clathrin coat and dynamin-1 to make an endosomal vesicle (Slepnev, V. I. et al., *Science*, 281:821–824 (1998); Shupliakov, O., et al., *Science*, 276:259–263 (1997); McMahon, H. T. et al., *FEBS Lett.*, 413:319–322 (1997); David, C., et al., *Proc. Natl. Acad. Sci.*, 93:331–335 (1996); and Urrutia, R., et al., *Proc. Natl. Acad. Sci.*, 94:377–384 (1997)). The carboxyl-terminal domain of amphiphysin recruits GTPase dynamin to pinch off the coated buds (David, C., et al., *Proc. Natl. Acad. Sci.*, 93:331–335 (1996); and Urrutia, R., et al., *Proc. Natl. Acad. Sci.*, 94:377–384 (1997). Disruption of the interaction of amphiphysin with either dynamin or clathrin and AP-2 inhibits clathrin-mediated endocytosis (Slepnev, V. I. et al., *Science*, 281:821–824 (1998); Shupliakov, O., et al., *Science*, 276:259–263 (1997); and Wigge, P. et al., *Curr. Biol.*, 7:554–560 (1997)). These findings indicate that amphiphysin may act as a regulated liner protein that couples clathrin-mediated budding of endocytotic vesicles to dynamin-mediated vesicle fission. Furthermore, it have been reported that amphiphysin has several subtypes and amphiphysin-2 also has a SH3 domain and has a binding-affinity to dynamin as amphiphysin-1.

Caveolae are vesicular invaginations of the plasma membrane with a diameter of 50–100 nm and are involved in endocytosis such as transcytosis and ptocytosis and signal transduction (Engelman, J. A. et al., FEBS Lett., 428:205 (1998)). Caveolin, a 21–24 kDa integral membrane protein, is a principal structural component of caveolae membranes in vivo. The stable expression of caveolin-1 or -3 gene to the mammalian cells without caveolin induced the formation of caveolae structures (Lipardi, C. et al., *J. Cell Biol.*, 140:617 (1998)). Caveolin has been found as several subtypes in vivo. Caveolin-1 is a key constituent of caveolae structures. Caveolin-2, is expressed ubiquitously in most cell types, supposedly forming a hetero-oligomer in basolaterally localized caveolae (Scheiffele, P. et al., *J. Cell Biol.*, 140:795 (1998)). It has been reported that the expression of caveolin-3 is restricted to striated muscle cells (Tang, Z. et al., J. Biol. Chem., 271:2255 (1996)).

I. Method for Detecting a Senescent Cell and Method for Identifying a Substance Affecting Cellular Senescence The present methods employ proteins involved in endocytosis such as amphiphysin protein and caveolin protein.

In the present method, the signal indicating cell senescence is detected either by measuring the decreased level of, amphiphysin protein in cell or by measuring the increased level of caveolin protein in cell.

The term "senescence" is used herein to have the same meaning as "aging." The term "old cell" is used herein to have the same meaning as "senescent cell." Unless otherwise defined, all technical and scientific terms used herein have the same meaning as commonly understood by one of ordinary skill in the art to which this invention belongs. For example, the terms used herein may be found in Benjamin Lewin, *Genes VII*, published by Oxford University Press (2000); and Kendrew et al., *The Encyclopedia of Molecular Biology*, published by Blackwell Science Ltd. (1994).

According to the preferred embodiment, the cell is derived from mammalian cell such as human cell.

Amphiphysin used in this invention may be selected from amphiphysin subtypes as described above. It is preferred that the amphiphysin protein is amphyamphiphysin-1, which has been known to a main subtype as mentioned previously. Furthermore, the caveolin protein used may be selected from caveolin-1, caveolin-2 and caveolin-3. It is preferred that the caveolin used is caveolin-1 protein, which has also been known to a main subtype as described previously.

In the present method which uses antibody against amphiphysin or caveolin, the antibody may be obtained as methods known to those skilled in the art (Antibodies: A Laboratory Manual, Cold Spring Harbor Laboratory (1988)). The antibody may be polyclonal or monoclonal antibody. Monoclonal antibody may be readily prepared through use of well-known techniques, such as those exemplified in U.S. Pat. No. 4,196,265. The step of determining the amount of the isolated protein bound to the antibody may be performed according to methods known to those skilled in the art such as radioimmunoassay and enzyme-linked immunosorbent assay. These methods are generally based on the detection of a label or marker such as radioactive, fluorescent, biological or enzymatic tags or labels.

In a preferred embodiment of this method, the method is conducted by western blotting method. The general procedure of western blottingmethod is disclosed in Peter B. Kaufma et al., *Molecular and Cellular Methods in Biology and Medicine*, 108–121, CRC Press. The western blotting for this invention, preferably, comprises the steps of (a) lysing a cell sample to be measured; (b) preparing a protein from the lysed cell; (c) denaturating the prepared protein in solution containing SDS and 2-mercaptoethanol; (d) performing SDS-polyacrylamide gel electrophoresis; (e) transferrin the protein on gel to nitrocellulose (hereinafter referred to as "NC") membrane; (f) reacting the protein on NC membrane with a primary antibody to amphiphysin or caveolin, advantageously, amphiphysin-1 or caveolin-1; (g) reacting the primary antibody with a secondary antibody conjugated to enzyme catalyzing calorimetric reaction; (h) inducing the calorimetric reaction by adding a substrate for the enzyme of (g); and (i) measuring the intensity of color developed by the enzyme (g).

Preferred enzyme for colorimetric reaction includes, but not limited to, alkaline phosphatase, β-galactosidase, and horse radish peroxidase. Where using alkaline phosphatase, bromochloroindolylphosphate (BCIP), nitro blue tetrazolium (NBT) and ECF may be used as a substrate; in the case of using horse radish peroxidase, chloronaphtol, aminoethylcarbazol, diaminobenzidine and luminol may be used as a substrate.

As described in Examples, the inventors have found that the level of amphiphysin in cell is dramatically decreased in senescent stage and vice versa for caveolin. Therefore, the present method may be carried out qualitatively. For example, the strength and the thickness of western blotting band for detecting amphiphysin may be found to be dramatically decreased to the extent capable of detecting visually; in the case of western blotting for detecting caveolin, the strength and the thickness of the resulting band may be found to be dramatically increased. Consequently, with comparing the western blotting band derived from senescent cell to one derived from young cell, the senescence can be easily detected.

Moreover, the present method may be carried out in a quantitative manner. For example, the bands resulted from western blotting may be transformed to quantitative data with densitometor. In a specific example for analyzing 40 μg protein, if the level of expression of amphiphysin-1 in tested cell is 45 times less than young cell, the tested cell may be considered senescent.

The present methods employ a polynucleotide coding for proteins involved in endocytosis such as amphiphysin protein and caveolin protein.

In this method, the signal indicating cell senescence is detected either by measuring the decreased level of a polynucleotide encoding amphiphysin protein in cell or by measuring the increased level of a polynucleotide encoding caveolin protein in cell.

Accoriding to the preferred embodiment, the cell is derived from mammalian cell such as human cell. It is preferred that the polynucleotide is one conding for amphiphysin-1 or caveolin-1 protein. It is preferred that the polynucletide used in this method is gDNA (genomic DNA), cDNA and mRNA.

In a preferred embodiment of this method, the method may be conducted by northern blotting method. The general procedure of northern blotting method is disclosed in Peter B. Kaufma et al., *Molecular and Cellular Methods in Biology and Medicine*, 102–108, CRC Press. The northern blotting for this invention, preferably, comprises the steps of (a) preparing RNA from cell to be tested; (b) performing electrophoresis with the prepared RNA; (c) transferrin the RNA to nylon or NC membrane; (f) hybridizing the transferred RNA with radio-labeled oligonucleotide probe complementary to amphiphysin mRNA or caveolin mRNA, advantageously, amphiphysin-1 or caveolin-1; and (g) measuring the intensity of the resulting band.

As described in Examples, the inventors have revealed that the level of amphiphysin RNA in cell is dramatically decreased in senescent stage and vice versa for caveolin. Therefore, the present method may be carried out qualitatively. For example, the strength and the thickness of northern blotting band for detecting amphiphysin RNA may be found to be dramatically decreased to the extent capable of detecting visually; in the case of northern blotting for detecting caveolin RNA, the strength and the thickness of the resulting band may be found to be dramatically increased. Consequently, with comparing the northern blotting band derived from senescent cell to one derived from young cell, the senescence can be conveniently detected.

Moreover, the present method may be carried out in a quantitative manner. For example, the bands resulted from northern blotting may be transformed to quantitative data with densitometor. In a specific example for analyzing 50 μg of amphiphysin-1 RNA, if the strength of band for tested cell is 15 times less than young cell, the tested cell may be considered senescent.

II. Composition for Modulating Cellular Senescence

The composition for modulating cellular senescence of this invention comprises biomolecule capable of modulating cellular senescence. The biomolecule includes: (a) protein such as amphiphysin protein and caveolin protein; and (b) a polynucleotide such as one encoding amphiphysin protein or caveolin protein. In addition, the biomolecule includes antisense oligonucleotide capable of hybridizing to a polynucleotide encoding amphiphysin protein or caveolin protein. Meanwhile, the composition of this invention comprises a methylating agent or a demethylating agent to methylate or demethylate bases of a polynucleotide encoding caveolin protein.

As described above, while it is conceivable that the proteins may be delivered directly, a preferred embodiment involves providing a polynucleotide encoding amphiphysin or caveolin.

According to the preferred embodiment, the cell is derived from mammalian cell such as human cell. It is preferred that the protein involve in endocytosis is amphiphysin-1 or caveolin-1 protein.

In the composition containing a polynucleotide, it is preferred that the polynucletide is gDNA or cDNA and is carried by expression vector for eucaryotic cell. The polynucleotide encoding amphiphysin-1 includes, preferably, nucleotide sequence coding for amino acids sequence represented by SEQ ID NO:2 and, more preferably, nucleotide sequence corresponding to nucleotides 111–2195 of nucleotide sequence represented by SEQ ID NO:1. The polynucleotide encoding caveolin-1 includes, preferably, nucleotide sequence coding for amino acids sequence represented by SEQ ID NO:4 and, more preferably, nucleotide sequence corresponding to nucleotides 26–559 of nucleotide sequence represented by SEQ ID NO:3.

The expression vector used in this invention expresses foreign gene in eucaryotic host, preferably mammalian cell, more preferably human cell. The promoter in the expression vector may be derived from the genome of mammalian cells (e.g., metallothionein promoter) or from mammalian viruses (e.g., adenovirus late promoter; vaccinia virus 7.5K promoter). Further, it is also possible, and may be desirable, to utilize promoter or control sequences normally associated with the desired gene sequence, provided such control sequences are compatible with the host cell systems. A number of viral based expression systems may be utilized, for example, commonly used promoters are derived from polyoma, Adenovirus 2, and most frequently Simian Virus 40 (SV40). It is desired to incorporate into the transcriptional unit an appropriate polyadenylation site. The example of commercial vectors used for this invention includes pcDNA 3 (Invitrogen; containing cytomegalo virus promoter and polyadenylation signal), pSI (Promega; containing SV 40 promoter and polyadenylation signal), pCI (Promega; containing containing cytomegalo virus promoter and polyadenylation signal), and pREP7 (Invitrogen; RSV promoter and SV 40 polyadenylation signal).

Furthermore, in the composition containing a polynucleotide encoding amphiphysin or caveolin, the polynucleotide may be delivered using viral vectors designed for gene therapy. For example, the delivery systems includes, but not limited to, (a) adenoviral vectors (Stratford-Perricaudet and Perricaudet, In: *Human Gene Transfer*, Eds., Cohen-Haguenauer and Boiron, Editions John Libbey Eurotest, France, 51–61 (1991); and Stratford-Perricaudet et al., *Hum. Gene Ther.*, 1:241–256 (1991)); (b) adeno-associated virus vectors (LaFace et al., *Virology*, 162:483–486 (1998); Zhou et al., *Exp. Hematol.*, 21:928–933 (1993); and Walsh et al., *J. Clin. Invest.*, 94:1440–1448 (1994)); and (c) retroviral vectors such as engineered variant of the Moloney murine leukemia virus (Kasahara et al., *Science*, 266:1373–1376 (1994)).

In the present composition containing antisense oligonucleotide, the antisense oligonucleotide may hybridize, under intracellular conditions, to target DNA or RNA. Targeting double-stranded DNA with an antisense oligonucleotide leads to triple-helix formation; targeting RNA leads to double-helix formation. Antisense oligonucleotide may be designed to bind to the promoter and other control regions, exons and introns of target gene. The antisense oligonucleotide used in this invention may be substantially complementary to target polynucleotide. That is, the antisense constuct may have some base mismatches to target gene. It is more preferred that the antisense oligonucleotide hybridizes to a polynucleotied encoding caveolin protein, advantageously, caveolin-1 protein. It is the most preferred that the antisense oligonucleotide hybridizes to translational initiation region of caveolin-1 mRNA.

In the present invention containing a methylating agent or a demethylating agent, the agent regulates the level of methylation for bases of caveolin gene. As described in Example, caveolin gene with less methylation level exhibits greater expression level. In a preferred embodiment, the caveolin gene to be methlyated or demethylated is caveolin-1 gene. More preferably, the modified region is a promoter of caveolin-1 gene and the most preferably, CpG island from the promoter of caveolin-1 gene. Example of methylating agent used in this invention includes, but not limited to, methylazoxymethanol acetate, Temozolomide and N-methyl-N-nitrosourea. Non-limiting example of demethylating agent used in this invention includes 5-aza-deoxycytidine, 5-azacytidine, 6-azacytidine and 8-azaguanine.

As a composition for modulating cellular senescence, the present invention provides a composition comprising the effective amount of dominant negative amphiphysin-1 gene. The dominant negative amphiphysin-1 gene, which has been known to block the function of amphiphysin-1 (Shupliakov, O. et al., *Science*, 276:259 (1997); and Wigge P., *Curr. Biol.*, 7:554 (1997)). The treatment with dominant negative amphiphysin-1 gene leads to cellular senescence as described in Example. According to a preferred embodiment, the dominant negative amphiphysin-1 gene is a polynucleotide encoding a polypeptide comprising the amino acid sequence 250 to 588 represented by SEQ ID NO:2.

III. Method for Modulating Cellular Senescence

In the method of this invention, the effective amount of biomolecule related to amphiphysin or caveolin is typically administered to a cell. In particular, a polynucleotide encoding amphiphysin or caveolin or antisense oligonucleotide thereof may be introduced in vivo or ex vivo in accordance with the following methods: (a) microinjection (Capecchi, M. R., *Cell*, 22:479 (1980)); (b) calcium phosphate co-precipitation (Graham, F. L. et al., *Virology*, 52:456 (1973)); (c) electroporation (Neumann, E. et al., *EMBO J.*, 1:841 (1982)); (d) liposome-mediated transfection (Wong, T. K. et al., *Gene*, 10:87 (1980)); (e) DEAE-dextran treatment (Gopal, *Mol. Cell Biol.*, 5:1188–1190 (1985)); and (f) particle bombardment (Yang et al., *Proc. Natl. Acad. Sci.*, 87:9568–9572 (1990)).

According to a preferred embodiment, the cell used is derived from mammalian cell, more preferred, human cell. Preferably, protein, polynucleotide and antisense oligonucleotide administered are related to amphiphysin-1 or caveolin-1. It is preferred that the polynucleotide administered is gDNA or cDNA. More preferably, the polynucleotide administered is carried on expression vector for eucaryotic cell. In a preferred embodiment of a method using antisense construct, the antisense oligonucleotide is substantially complementary to the gene encoding caveolin, more preferably, caveolin-1. The most preferable embodiment comprises the antisense oligonucleotide hybridizes to translational initiation region of caveolin-1 mRNA.

In the present method using a methylating agent or a demethylating agent, the agent regulates the level of methylation for bases of caveolin gene. In a preferred embodiment, the caveolin gene to be methlyated or demethylated is caveolin-1 gene. More preferably, the modified region is a promoter of caveolin-1 gene and the most preferably, CpG island from the promoter of caveolin-1 gene. Example of methylating agent used in this invention includes, but not limited to, methylazoxymethanol acetate, Temozolomide and N-methyl-N-nitrosourea. Non-limiting example of demethylating agent used in this invention includes 5-aza-deoxycytidine, S-azacytidine, 6-azacytidine and 8-azaguanine.

The common descriptions of between I, II and III are abbreviated in order to avoid the complexity of this specification leading to undue multiplicity.

IV. Kits and Biomarkers

As indicated above, the present invention provides a kit for detecting a senescent cell. All the essential materials and reagents required for detecting a senescent cell may be assembled together in a kit. The probe used may be useful for hybridization to DNA or RNA isolated from a cell to be tested. Furthermore, the probe used may be primer primer for use in any molecular biology assay known to those of skill in the art such as PCR and RT-PCR. Also included may be enzymes suitable for amplification nucleic acids such as Taq polymerase, dNTP mixture and buffers to provide the necessary reaction mixture for amplification.

In a preferred embodiment, the probe is derived from the polynucleotide encoding amphiphysin-1 protein or caveolin-1 protein. The probe, preferably, is immobilized on a solid support. Solid supports suitable for use in the kit of this invention are known to those of skill of the art, which includes glasses, plastics, polymers, metals, metalloids, ceramics and organics. According to more preferred embodiment, this invention provides a kit comprising an array of probes derived from the polynucleotide encoding amphiphysin-1 protein or caveolin-1 protein. The general techniques for microarray containing solid supports have been disclosed in many publications such as WO 89/10977, U.S. Pat. Nos. 5,202,231, 5,002,867 and 5,143,854.

According to preferred embodiment of this invention, the kit further comprises a label for detecting the presence of the probe. The label allows detection of hybridization of between the probe and nucleotides isolated from sample to be tested. The most common label is radioactive material such as $^3H$, $^{14}C$ and $^{32}P$.

The present invention provides a biomarker for identifying cellular senescence. In preferred embodiments, the protein or the polynucleotie suitable for this invention, is derived from amphiphysin-1 or caveolin-1.

The following specific examples are intended to be illustrative of the invention and should not be construed as limiting the scope of the invention as defined by appended claims.

EXAMPLE I

Cell Culture

I-1: Culture for Human Foreskin Fibroblast

Foreskin fibroblast was isolated and cultured according to the method provided by Boyce and Ham (Boyce ST. and Ham R G., *J. Invest. Dermato.*, 81:33–40 (1983)) as follows: First, foreskin was obtained from 7-year-old Korean male and was stripped to give pieces, after which the foreskin pieces was added to 10 ml of Hank's salt solution (Gibco BRL) containing 0.25% collagenase. Following incubating for 90 min. at 37° C. in $CO_2$-controlled (5%) incubator, epithelium and dermis were separated from each other. To the separated dermis, 1 ml of trypsin solution (0.25%) was added and the resulting solution was added to 10 ml of DMEM (Dulbecco's modified Eagle medium: Sigma) containing 100 μg/ml of streptomycin and 100 units/ml of penicillin, followed by incubating for 10 min. at 37° C. The yielded foreskin fibroblast were washed with 10 ml of PBS and in DMEM (supplemented with 10% FBS and antibiotics) were serially passaged as follows: The incubator was maintained to the atmosphere of 5% $CO_2$ and the temperature of 37° C., DMEM was renewed once per 3 days and subconfluency (about 80–90%) was kept and subculture was performed at a 1:4 ratio. The cells, cultured with less than 25 population doublings, were considered presenescent cells (or young cells), which are highly proliferative, while cells with over 60 population doublings were defined as senescent cells, which showed delayed population doublings times (over 3 weeks).

I-2: Culture for Fetal Lung Fibroblast

Fetal lung fibroblast, IMR-90, was purchased from ATCC (CCL-186). The culture for IMR-90 was carried out in the same manner as the above.

EXAMPLE II

Induction of Cellular Senescence

II-1: Induction of Cellular senescence with $H_2O_2$

The fibroblasts subcultured in Exmaple I-1, PDL of which are 16, were placed in culture plate and were kept to arrest cell cycle to Gi phase in incubator (37° C., 5% $CO_2$ and humidified) for a week. The cell cycle arrest was confirmed as follows: Following the fixation of the cells with cold ethanol, the cells were stained for 30 min. at room temperature using PI staining solution (containing 50 μg/ml of Rnase A and 50 μg/ml of propinium iodide in PBS). Thereafter, using FACS (fluorescence-activated cell sorter), the cell cycle was confirmed by observing DNA phenotype, i.e., 2n or 4n. The cells in G1 phase were showed 2n of DNA phenotype.

The fibroblasts arrested in G1 phase were treated with 400 μM $H_2O_2$ and then incubated for 3 hrs., followed by washing with 10 ml of PBS. Then, the cells were subcultured at a 1:4 ratio and under normal conditions for cell culure (37° C., 5% $CO_2$ and humidified), cell culture was continuously performed. Following 7 days after the treatment, the cells were determined in terms of senescence using senescence-associated β-galactosidase activity staining as described in Example III.

II-2: Induction of Cellular senescence with Hydroxyurea

The fibroblasts subcultured in Exmaple I-1, PDL of which are 16, were placed in culture plate containing DMEM and were cultured in incubator (37° C., 5% $CO_2$ and humidified) for 14 hrs. Thereafter, the fibroblasts were treated with 400 μM Hydroxyurea and then incubated continuously. The medium was renewed once per 3 days with the addition of fresh 400 μM Hydroxyurea. Following 14 days after the treatment, the cells were determined in terms of senescence using senescence-associated β-galactosidase activity staining as described in Example III.

EXAMPLE III Senescence-Associated β-Galactosidase Activity Staining

A senescence-associated β-galactosidase activity staining (hereinafter referred to as "SA β-gal activity staining") was performed according to the method of Dimri et al. (Dimri GP et al., Proc. Natl. Acad. Sci., 92:9363 (1995)): The semiconfluent fibroblasts were washed twice with 10 ml of PBS and fixed with 2% paraformaldehyde in PBS for 5 min. at room temperature. After washing with PBS, cells were incubated with SA β-gal activity staining solution (1 mg/ml of X-gal, 40 mM citric acid/sodium phosphate buffer, pH 6.0, 5 mM potassium ferrocyanide/ferricyanide, 150 mM NaCl and 2 mM $MgCl_2$) at 37° C. for 4 hrs. Young and old human fibroblasts were observed with phase contrast microscopy. As a result of the observation, human fibroblast showed β-galactosidase activity from PDL 50, IMR 90 from PDL 65, cells treated with $H_2O_2$ from 10 days after treatment and cells treated with hydroxyurea from 14–20 days after treatment, which demonstrate the entry of cellular senescence.

EXAMPLE IV

Evaluation of Alteration of Endocytosis

IV-1; Observation of Reduced Endocytosis in Senescent Cell

To investigate the functional changes of receptor-mediated endocytosis in senescent cell, the internalization of transferrin was observed. The fibroblasts were plated onto cover glasses and incubated in incubator (37° C., 5% $CO_2$ and humidified), followed by the treatment of 25 μg/ml tetramethylrhodamine-conjugated human transferrin (Molecular Probes) for 5 min. After washing 10 ml of PBS, the cells were fixed with 4% paraformaldehyde in PBS for 10 min at room temperature, and then, nuclei of cells were stained with DAPI (Sigma Aldrich). Internalization of fluorescent transferrin was monitored with confocal microscopy (Biorad, #MRC1024). Young fibroblasts and IMR cells took up fluorescent transferrin readily and internalized transferrin was observed as typical punctuated crescent shapes in the perinuclear area. In contrast, senescent cells did not uptake transferrin as efficiently as presenescent cells.

IV-2: Observation of Internalization of Transferrin with Increase of Treatment Time The fibroblasts were treated with 25 μg/ml tetramethylrhodamine-conjugated human transferrin for 10, 20, 40 or 60 min as described previously. Cells with PDL 24 and PDL 38 took up fluorescent transferrin efficiently and internalized transferrin was observed in the perinuclear area in 10-min treatment, which was increased with the increase of treatment time, thereby giving greater fluorescence intensity. In contrary to this, the senescent fibroblasts did not uptake transferrin even after 60-min treatment.

IV-3: Pulse-Chasing of Transferrin Uptake

Twenty five μg/ml rhodamine-conjugated transferrin was pulsed on IMR 90 cells for 5 min and then chased for 0, 5 and 10 min. After fixing as described above, internalization of fluorescent transferrin was monitored with confocal microscopy. Young cells efficiently uptake transferrin and localize it to perinuclear area just in 5 min and then the transferrin was quickly degraded after 10 min chasing. PDL 48 cells revealed a delayed and limited uptake of transferrin after 10 min chasing. PDL 72 cells nearly failed to uptake transferrin with the lapse of chasing time.

IV-4: Observation of Reduced Endocytosis in Artificially Induced Senescent Cell

The senescent cells which were artificially induced in Example II were treated with 25 μg/ml rhodamine-conjugated transferrin as above and internalization of fluorescent transferrin was monitored with confocal microscopy. Not only naturally-occurring senescent cells through serial passage but also artificially-induced senescent cells by $H_2O_2$ or hydroxyurea showed the reduced function of receptor-mediated endocytosis.

In summary, the inventors have revealed that senescent fibroblast cells show significantly reduced function of endocytosis and thus fail to uptake a variety of ligands such as transferrin.

EXAMPLE V

Analysis of Expression of Proteins Involved in Receptor-Mediated Endocytosis

To identify the molecular mechanism for such alteration in the receptor-mediated endocytosis of senescent cells, the expression level of several proteins involved in receptor-mediated endocytosis was checked through western blotting experiment.

Figure 5:
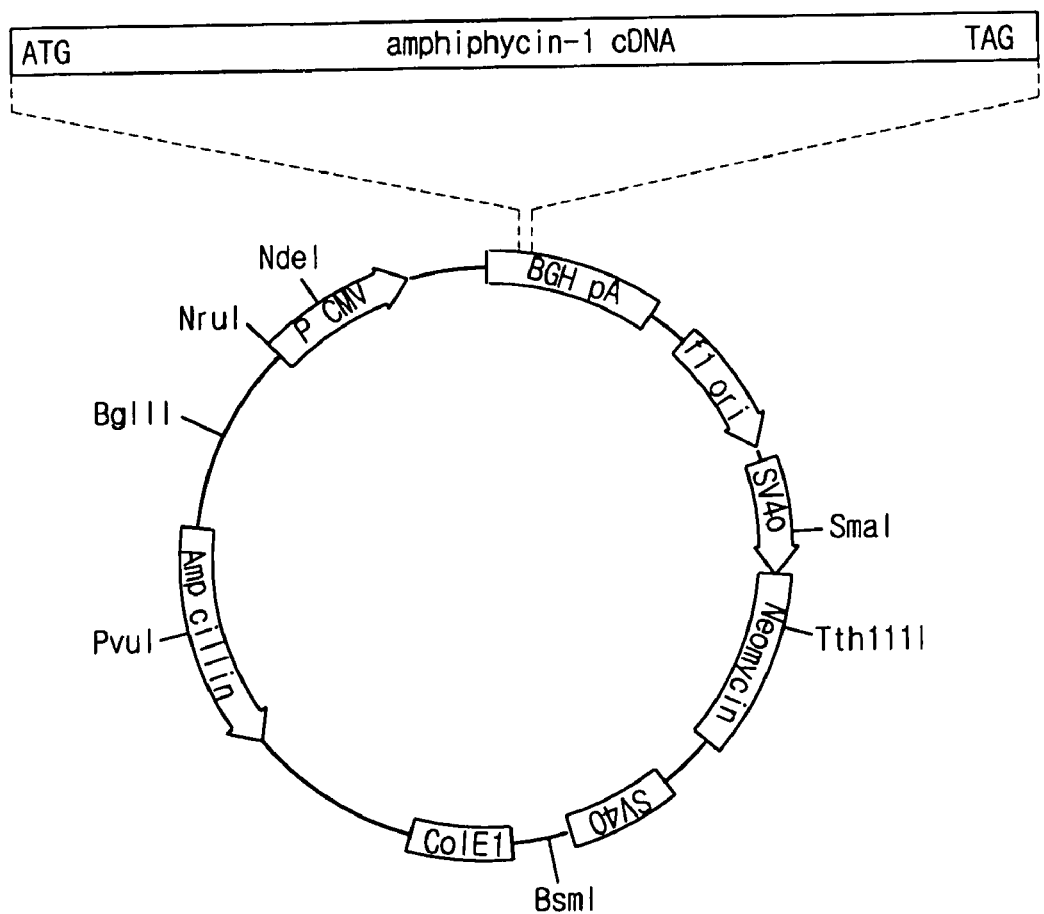
FIG. 5 shows a genetic map of the expression vector carrying cDNA encoding human amphiphysin-1 constructed in Example VII.

First, total cell lysates were extracted from subconfluent early, middle and late-passaged cells using lysis buffer (1% Triton X-100, 0.5% NP-40, 50 mM Tris pH7.5, 150 mM NaCl, 1 mM EDTA, 1 mM PMSF, 5 μg/ml aprotinin, 5 μg/ml leupeptin, 1 mM $NaVO_4$ and 1 mM NaF) and sonicated briefly, after which the lysates were centrifuged at 14000×g for 10 min and the supernatants were taken. With the supernatants, the protein quantification was performed as Bradford method (Bradford, M., Anal. *Biochem.* 0.72:248–254 (1976)) and 40 μg of protein equivalents were boiled for 5 min in 5× SDS sample buffer (60 mM Tris-Cl, pH 6.8, 25% glycerol, 2% SDS, 14.4 mM 2-mercaptoethanol and 0.1% bromophenol blue). Cell lysates (10–15 μg of protein equivalents) were electrophoresd on 8% polyacrylamide gel using electrophoresis kit (Biorad) and then transferred to nitrocellulose membranes using transfer kit (Biorad). The blots were blocked with TTBS (Tris buffered saline with Tween 20) containing 5% non-fat dry milk (Difco) for 1 hr at room temperature. The blots were immunoblotted with the respective primary antibody in TTBS with 5% non-fat dry milk for 1 hr. at room temperature, washed three times with TTBS, and incubated with horseradish peroxidase-conjugated anti-mouse secondary antibody (Jackson Immuno Research Laboratory). In the primary antibodies, anti-dynamin antibody, anti-α-adaptin, anti-β-adaptin and anti-clathrin heavy chain antibody were purchased from Transduction Laboratories, monoclonal antibody to amphiphysin-1 was prepared by Dr. Kim from Chungbuk National University (Jin, Y., Kim et al. (In press), Production and characterization of monoclonal antibodies against amphiphysin, *Exp. Mol. Med.*), and anti-phosphotyrosin antibody and anti-transferrin receptor antibody were Santa Cruz Biotechnology. The signals were finally visualized by an enhanced chemiluminescence system (ECL kit, Amersham Pharmaca Biotech), which are found in FIG. 5.

Figure 2:
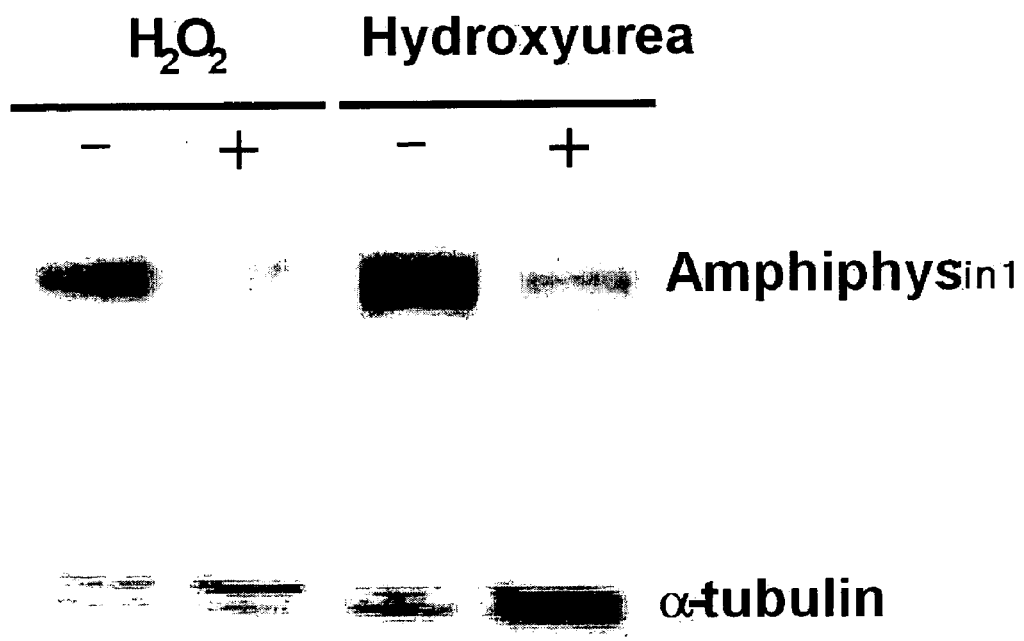
FIG. 2 is a photograph showing the results of western blotting for analyzing the expression of proteins associated with cellular senescence in induced senescent cell by $H_2O_2$ or hydroxyurea.

As demonstrated in FIG. 1, only amphiphysin-1, but none of other endocytotic protein tested, was significantly reduced in senescent cells. The unique reduction in expression of amphiphysin-1 protein was observed in the senescent cells of both foreskin fibroblasts and IMR 90 cells. Moreover, the senescent cells which were induced by $H_2O_2$ or hydroxyurea (marked "+") gave the same results as shown in FIG. 1 (see FIG. 2).

These results indicate that the cellular senescence process is accompanied with down regulation of amphiphysin-1.

EXAMPLE VI

Figure 3:
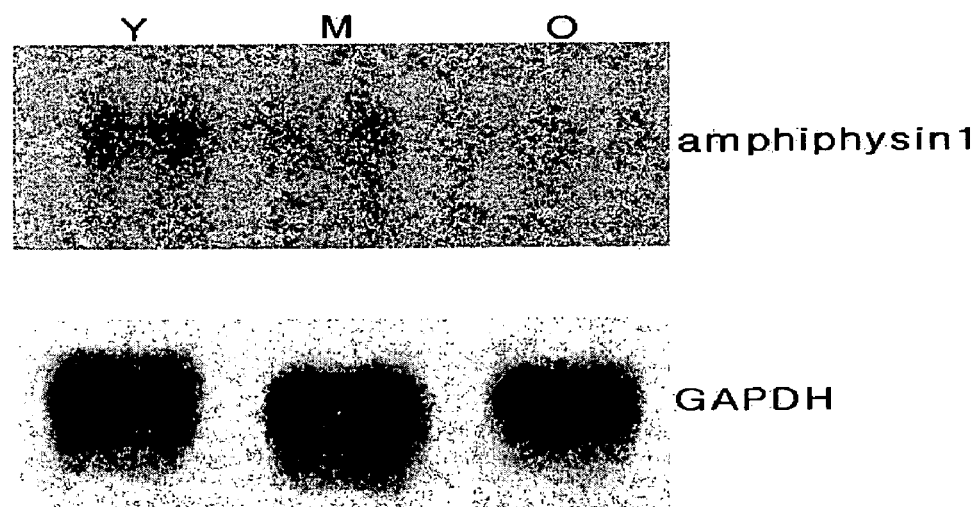
FIG. 3 is a photograph showing the results of northern blotting for analyzing mRNA encoding proteins associated with cellular senscense.

Northern Analysis of mRNA Encoding Proteins Involved in Receptor-Mediated Endocytosis To investigate the exact mechanism for the reduced level of amphiphysin-1 protein in senescent cells, which was analyses in Example V, northern blotting was carried out as follows:

The RNA was isolated from human fibroblasts of Example I using acid guanidinium thiocyanate-phenol-chloroform, mixed with formaldehyde sample buffer (5× MOPS, 17.5% formaldehyde and 50% formamide), and then electrophoresed on 1% agarose gel using electrophoresis kit (Hoefer). Following the electrophoresis, the RNA was transferred to nitrocellulose membrane and was cross-linked to the membrane using auto UV crosslinker (Stratagen). Then, the hybridization was performed with $p^{32}$-labelled probe (comprising bases 111–1116 of amphiphysin-1 cDNA) and the resulting autoradiograms were obtained (see FIG. 3). In FIG. 3, panels Y, M and O represent PDL 27, PDL 36 and PDL 60 fibroblasts, respectively. According to FIG. 3, it was elucidated that the level of amphiphysin mRNA was reduced with a progression of senescence.

Theses results indicate that the cellular senescence process is accompanied with down regulation of amphiphysin-1 at transcriptional level.

EXAMPLE VII

Cloning of Amphiphysin-1 Gene

Figure 4:
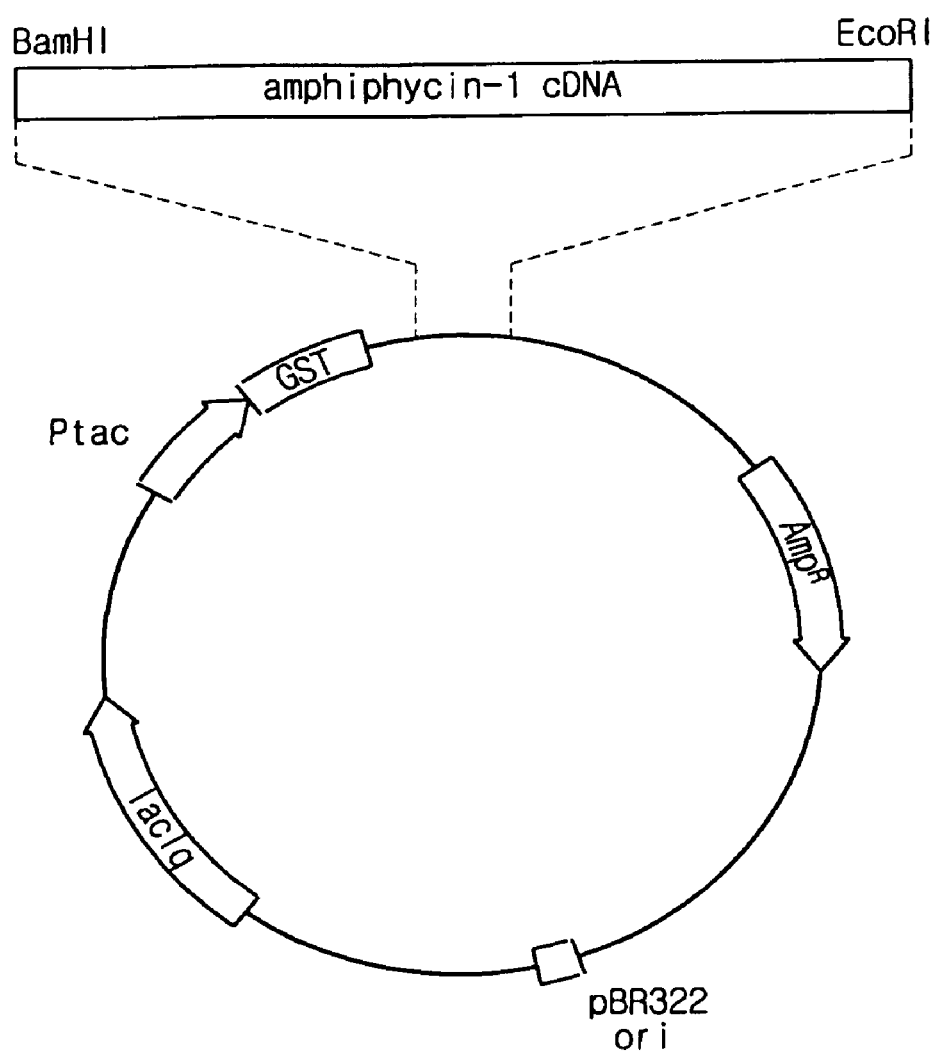
FIG. 4 shows a genetic map of the vector carrying cDNA encoding human amphiphysin-1 used in Example VII.

The cDNA encoding the full length of human amphiphysin-1 has a nucleotide sequence represented by SEQ ID NO:1 and the vector carrying the cDNA was obtained from Chungbuk National University (Korea). The vector was constructed in such a manner that the cDNA was inserted between BamHI and EcoRI restriction sites of pGEX-2T vector (Pharmacia) and thereby amphiphysin-1 and glutathione-S-transferase were expressed in fused form. FIG. 4 shows genetic map of the final vector carrying cDNA encoding human amphiphysin-1. The full length cDNA was amplified by PCR using a set of primers: 5'-AACTGTC-CACCATGGCCGACATCAAGACGGGC-3' (SEQ ID NO:5) and 5'-GGATCCCTAATCTAAGCGTCGGGT-3' (SEQ ID NO:6). The PCR amplification was performed for 30 cycles using Pyrobest Taq polymerase (Takara) in accordance with following temperature sets: 55□ for 30 sec (annealing), 72° C. for 1.5 min (extension) and 92° C. for 30 sec (denaturation). The amplified cDNA was cloned into pT7 blue vector (Novagen) and its base sequence was determined. After digestion with HindIII and BamHI, the cDNA was subcloned into pcDNA3 vector (Invitrogen: containing promoter and polyadenylation signal of cytomegalo virus) in order to microinject the amplified cDNA of amphiphysin-1 to fibroblast. The pcDNA3 containing cDNA of amphiphysin-1 was showed in the genetic map of FIG. 5.

Example VIII

Restoration of Endocytic Function in Senescent Cell by Amphiphysin-1 Gene

VIII-1: Microinjection of Amphiphysin-1 Gene

Senescent fibroblasts (PDL 58) in Example I were placed onto cover glass and incubated for 24 hrs. in DMEM with on FBS in incubator (37° C., 5% $CO_2$ and humidified). Then, $10^{-14}$ l of amphiphysin-1 gene cloned into pcDNA3 of Example VII (10 ng/ml) and $10^{-14}$ l of rabbit IgG (Sigma, 5 mg/ml) were microinjected into nucleus of senescent fibroblast. The vector was diluted to 10 ng/ml in the microinjection buffer (50 mM HEPES, pH 7.2, 100 mM KCl, 50 mM $NaPO_4$). The diluted vector was microinjected into nucleus using transjector 5426 (Eppendorf) and micromanipulator (Eppendorf).

VIII-2: Analysis of Amphiphysin-1 Expression in Microinjected Cell

Figure 6:
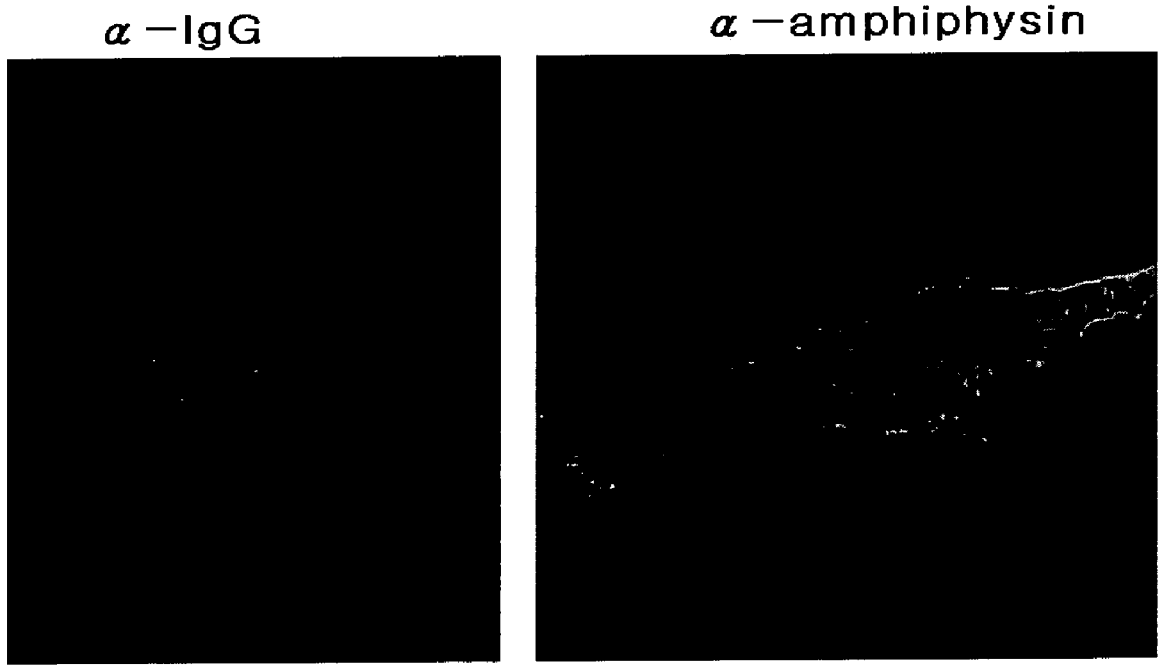
FIG. 6 shows a photograph representing image observed with fluorescence microscope for analyzing amphiphysin-1 expression in microinjected cells.
Figure 10:
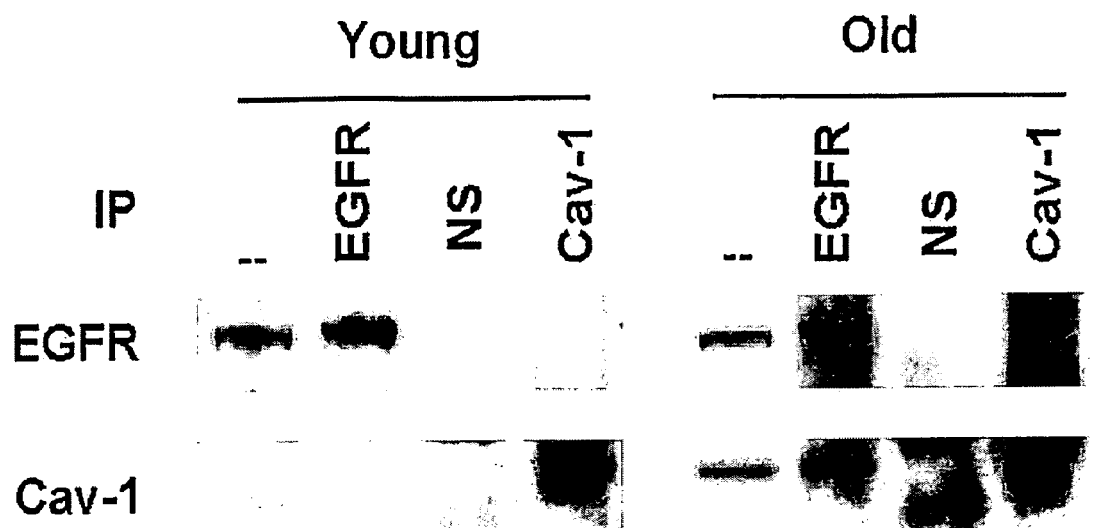
FIG. 10 shows a photograph representing the results of immunoprecipitation, which verifies the interaction between epidermal growth factor receptor (EGFR) and caveolin-1 in young and old cells.

Using double immunofluorescent staining method, the expression of amphiphysin-1 in microinjected cell was analyzed. Following 24 hrs. incubation in DMEM without FBS after microinjection, the cells were fixed with 3.7% paraformaldehyde (in PBS) for 10 min. and then permeabilized with 0.3% Triton X-100 in PBS for 10 min at room temperature. The cells were sequentially incubated with anti-amphiphysin-1 antibody, FITC-conjugated anti-rat IgG antibody (Jackson Laboratory: 1:100 dilution) for 1 hr at 37° C., and then rhodamine-conjugated anti-rabbit IgG antibody (Jackson Laboratory: 1:100 dilution) for 1 hr at 37° C. The image was observed with fluorescence microscope (Zeiss, Axiovert25, CFL451210) (see FIG. 10). As shown in FIG. 6, anti-rabbit IgG gives red fluorescence emitted by rhodamine and amphiphysin-1 is determined by green fluorescence emitted by FITC of secondary antibody. The green fluorescence demonstrating the existence of amphiphysin-1 was observed in cytoplasm.

Therefore, it is elucidated that amphiphysin-1 protein is expressed in the microinjected cells in Example VIII-1.

VIII-3: Analysis of Restoration of Endocytic Function in Senescent Cell

Microinjected cells were incubated for 24 hrs. in DMEM without FBS in incubator (37° C., 5% $CO_2$ and humidified). Then, the cells were treated with 125 ng/ml tetramethylrhodamine-conjugated transferrin for 30 min., washed with 10 ml of PBS and fixed with 10 ml of 4% formaldehyde (in PBS) for 10 min. The immunofluorescence staining was performed as described in Example VIII-2. By means of fluorescence microscope (Zeiss, Axiovert 100) microinjected cells and uptaken transferrin were analyzed. The results are summarized in Table 1.

TABLE 1

| | | Microinjected Cell | | | Non-Microinjected Cell | | |
|---|---|---|---|---|---|---|---|
| DNA[1] | Ab[2] | Tf[3] | Total[4] | Ave[5] (%) | Tf | Total | Ave (%) |
| PcDNA3 | Anti-rabbit IgG Ab | 1<br>1 | 12<br>15 | 7.50 | 4<br>3 | 32<br>31 | 11.09 |
| Ap-1[6] gene + pcDNA3 | Anti-rabbit IgG Ab | 1<br>1 | 12<br>15 | 7.50 | 18<br>10 | 46<br>29 | 36.81 |
| | Anti-amphiphysin-1 Ab | 1<br>2 | 12<br>16 | 10.42 | 18 | 37 | 48.65 |

[1] microinjected DNA;
[2] antibody for analyzing microinjected cell;
[3] transferrin;
[4] total cell number;
[5] average value; and
[6] amphiphysin-1.

As known in Table 1, compared to cells microinjected with pcDNA3 as mock, the microinjected cells with pcDNA3 carrying amphiphysin-1 gene shows much higher transferrin-uptake activity. In other words, the endocytic activity of senescent cells was sharply increased by the introduction of amphiphysin-1 cDNA. These results successfully demonstrate that amphiphysin-1 is essential for the restoration of functional endocytosis of the senescent cells and thus is essential for modulating cellular senescence.

EXAMPLE IX

Cloning of Dominant Negative Amphiphysin-1 Gene

Figure 7:
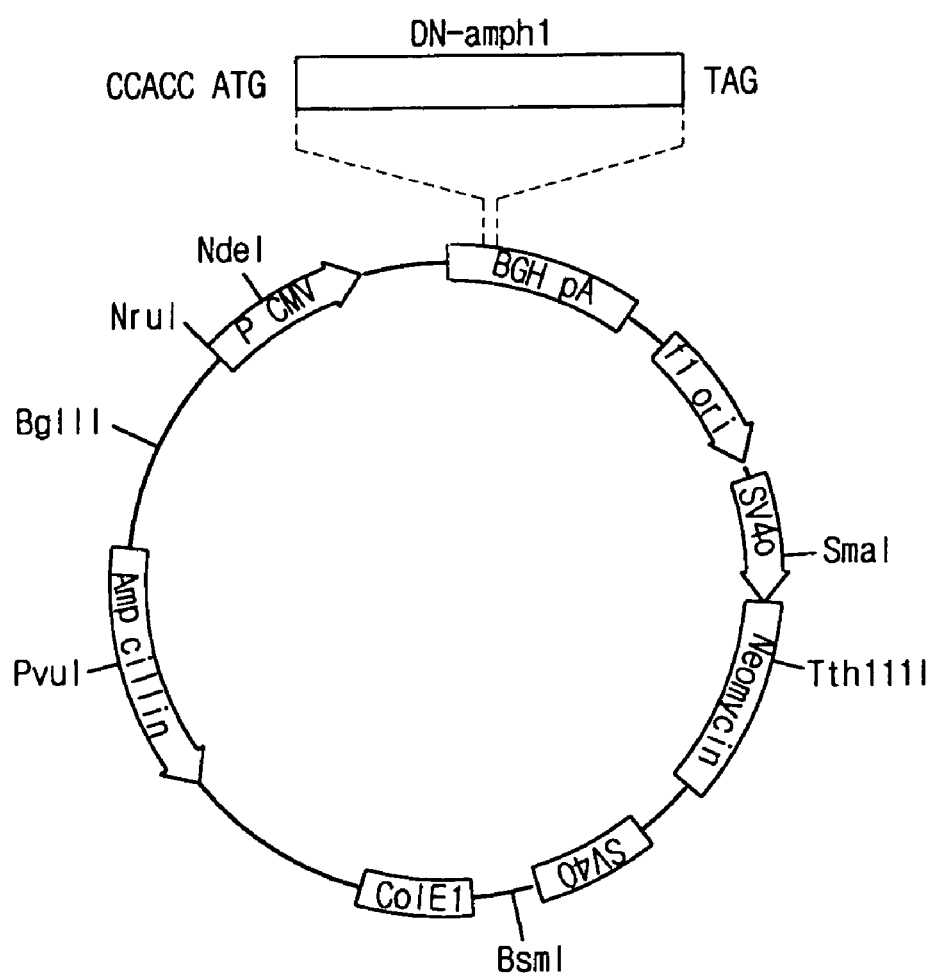
FIG. 7 represents a genetic map of the expression vector carrying dominant negative amphiphysin-1 gene.

Dominant negative amphiphysin-1 gene, which is known to block the function of amphiphysin-1 (Shupliakov, O. et al., Science, 276:259 (1997); and Wigge P., Curr. Biol., 7:554 (1997)), was amplified by PCT using amphiphysin-1 cDNA as template and specific primers, thereby amplifying a partial nucleotide sequence encoding the middle part of amphiphysin-1 protein (amino acids 250 to 588). The forward primer and reverse primer used have the following sequences: 5'-AACTGTCCACCATGAGTGATTCGGGTC-CTCTCCGC- 3' (SEQ ID NO:7) and 5'-GGATCCCTACT-GCTCCGTAGCCAGCTCCGG- 3'(SEQ ID NO:8), respectively. The PCR amplification was performed and the amplified product was subcloned using pcDNA 3 (Invitrogen) in the same manner as Example VII. The genetic map of the final vector is shown in FIG. 7.

EXAMPLE X

Suppression of Endocytic Function in Young Cell by Dominant Negative Amphiphysin-1 Gene Using the vector constructed in Example IX, young fibroblasts (PDL 16) were transformed as follows: Two μg of the vector constructed in Example IX and 0.5 μg of pEGFP-N1 vector (Clontech) were mixed with DMEM and 8 μl of Plus reagent, after which the resultant was allowed to stand for 15 min. at room temperature. Thereafter, the mixture was mixed well with Lipofectamine (Gibco-BRL) and DMEM, followed by standing the mixture for 15 min. at room temperature. Following the further addition of 2 ml of DMEM, the final mixture was added to young fibroblasts and then incubated for 3 hrs at 37° C. After the lapse of 3 hr., 2.5 ml of DMEM containing 20% FBS were added and incubated for another 40 hr. The incubated cells were treated with 25 μg/ml rhodamine-conjugated transferrin for 10 min. and the image was observed by confocal microscope (Biorad, #MRC1024), thereby elucidating the internalization of transferrin either in transformed cell (emitting EGFP-derived green fluorescence) or in non-transformed cell. Co-transformed cells with the vector carrying dominant negative amphiphysin-1 cDNA and pEGFP-N1 (left panel) show no red fluorescence by rhodamine-conjugated transferrin, indicating that the internalization of rhodamine-conjugated tansferrin does not occur, but non-transformed cells (right panel) show red fluorescence.

These results demonstrate that the functional incompetence of amphiphysin-1 can inhibit receptor-mediated endocytosis and finally induce cellular senescence.

EXAMPLE XI

Analysis of Erk-1/2 Activation by Western Blotting

Figure 8A:
FIG. 8a shows a photograph representing the results of western blotting for analyzing the activation (phosphorylation) of Erk-1/2 kinase in young and middle cells.
Figure 8B:
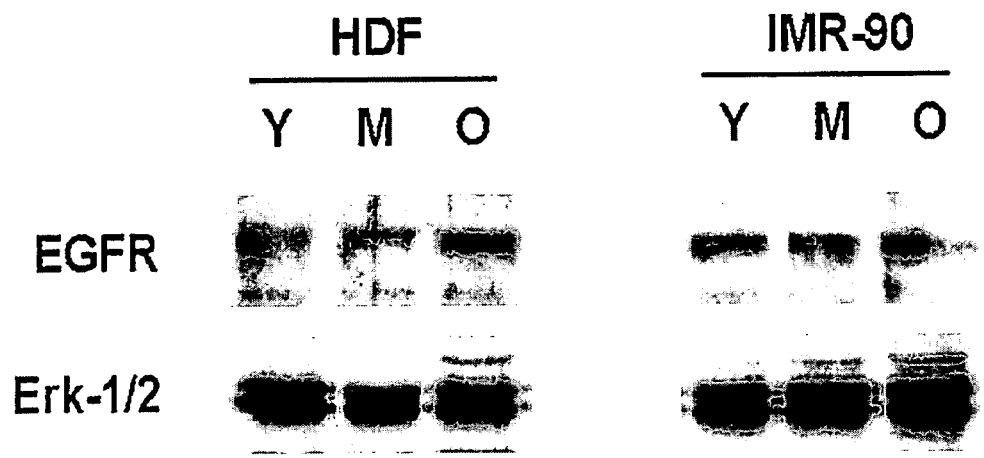
FIG. 8b shows a photograph representing the results of western blotting for analyzing the activation (phosphorylation) of Erk-1/2 kinase in old cells.

Young cells (PDL less than 30), middle cells (PDL 35–45) and old cells (PDL more than 60) of Human fibroblasts or IMR-90 cells, respectively were stimulated with 100 ng/ml EGF (Gibco-BRL, human, recombinant). After stimulation, western blotting was performed as described in Example V. Monoclonal anti-phospho-Erk-1/2 antibody, polyclonal anti-Erk-1/2 antibody and polyclonal anti-EGFR antibody were purchased from Santa Cruz Biotechnology, Inc. As found in FIG. 8a, in both young and middle-aged cells, Erk-1/2 kinases were phosphorylated (activated) within 5 min, and the resulting activation was sustained for 15 min after EGF stimulation. However, the phosphorylation of Erk-1/2 kinase from old cells was not detected until 15 min had lapsed. The expression level of Erk kinase and and EGFR was not changed by the increase of population doubling in Western blot (see FIG. 8b), despite the down-regulation of EGF signaling to Erk kinases.

Therefore, the reduced responsiveness of old cells to growth factor is due to the reduced Erk-1/2 phosphorylation, i.e., the reduced Erk-1/2 activation.

EXAMPLE XII

Analysis of Caveolin Expression by Western Blotting

Figure 9:
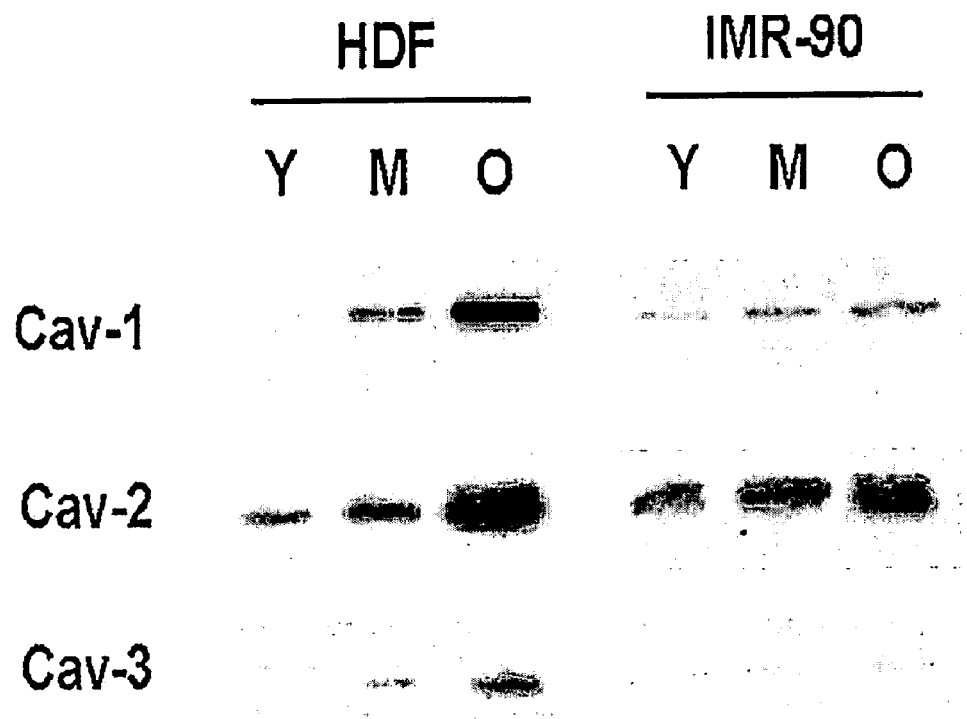
FIG. 9 shows a photograph representing the results of western blotting for analyzing the expression of caveolin subtypes, that is, caveolin-1, caveolin-2 and caveolin-3, in young, middle and old cells.

Analysis of caveolin expression, in young cells (PDL less than 30), middle cells (PDL 35–45) and old cells (PDL more than 60) of Human fibroblasts or IMR-90 cells, was performed by Western blotting as described in Example V. Monoclonal anti-caveolin-1 antibody, monoclonal anti-caveolin-2 antibody and monoclonal anti-caveolin-3 antibody were purchased from Transduction Laboratories. As shown in FIG. 9, with aging, all of caveolin-1, caveolin-2 and caveolin-3 were expressed increasingly in both human fibroblasts and IMR-90 cells.

EXAMPLE XIII

Analysis of Interaction between EGFR and Caveolin-1 by Immunoprecipitation

Young (PDL less than 30) or old (PDL more than 60) fibroblasts were lysed in IP lysis buffer (10 mM phosphate buffer, pH 7.4,150 mM NaCl, 1% Nonidet P-40, 2 mM EDTA, 1 mM phenylmethylsulfonyl fluoride, 2 μg/ml aprotinin, 2 μg/ml leupeptin, 50 mM NaF, 0.2 mM $Na_3VO_4$) and sonicated briefly. Lysates were spin down at 9,000 rpm for 5 min., and supernatants were incubated with normal mouse serum, anti-EGFR antibody or anti-caveolin-1 antibody. Immune complexes were precipitated with protein A-Sepharose beads (Amersham Pharmacia Biotech) and separated by SDS-polyarylamide gel electrophoresis and analyzed by Western blot as described in Example V (see FIG. 10).

Figure 15:
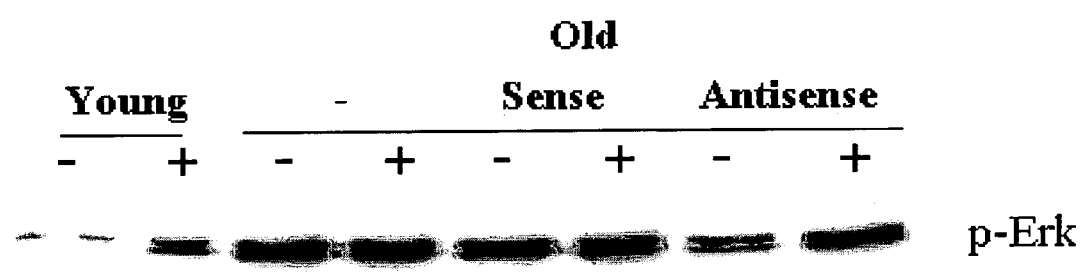
FIG. 15 is a photograph showing the results of western blotting for analyzing Erk-1/2 activation upon transfection of antisense oligonucleotie to caveolin-1.

As demonstrated in FIG. 15, the immune complex of EGFR from old fibroblasts contained caveolin-1 proteins, while young fibroblasts did not show a comparable amount of caveolin-1 and subsequent interactions with EGFR.

It is elucidated that with aging, the expression of caveolin-1 protein is increased and then the increased caveolin-1 protein is interacted with EGFR to inhibit the activation of Erk-1/2 kinase by EGFR.

EXAMPLE XIV

Electron Microscopic Analysis for Caveolin-1

Figure 11:
FIG. 11 is an electron microphotograph showing caveolae structure in young and old cells.

Subconfluent young (PDL 20) and old (PDL 65) fibroblasts were palletized by centrifugation (1,000 rpm) and fixed with 3% glutaraldehyde/phosphate-buffered saline at pH 7.4. After washing with 0.2 M sodium cacodylate buffer, pH 7.4, cell pellets were treated with 1% osmium tetroxide in cacodylate buffer for 1 hr. The cells were then dehydrated in graded ethanol steps through propylene oxide and embedded in Embed812 (Electron Microscope Sciences). The embedded cells were cut to the size of 200 nm by microtomb (Leichert-JUNG) and the cuts were stained with methylene blue and azure II, followed by observation with light microscopy in order to select the appropriate observation region of electron microscopy. Thereafter, the selected region was ultra-cut to the size of 60 nm by microtomb (Leichert-JUNG) and stained with uranyl acetate and lead citrate. Sections were observed using a transmission electron microscope (H-600, Hitachi). FIG. 11 indicates that old fibroblasts contain significantly more caveolae-like structure than young cells.

EXAMPLE XV

Construction of Plasmid DNA Carrying Caveolin-1 cDNA

Figures 12, 13:
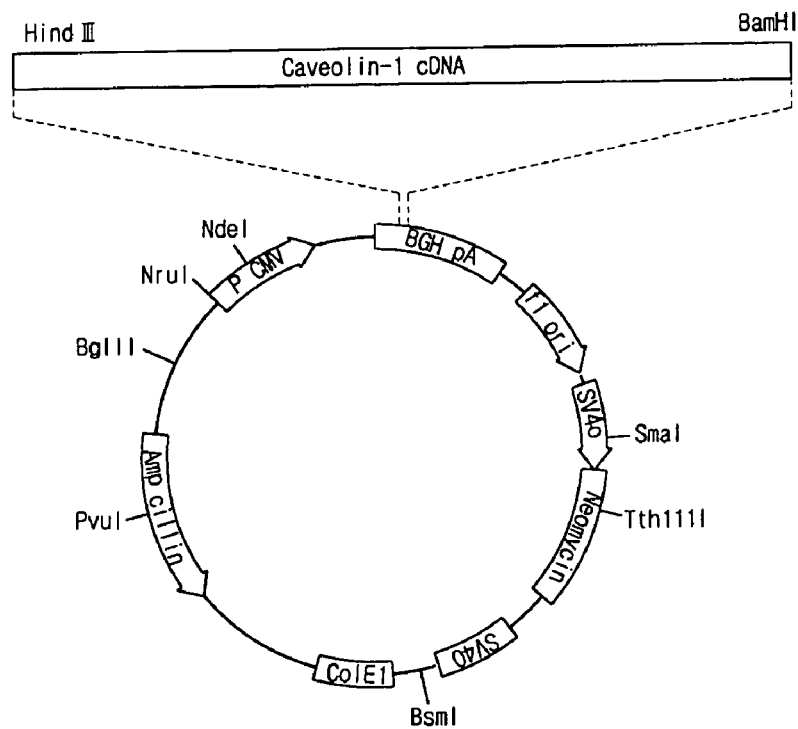
FIG. 12 represents a genetic map of the expression vector carrying caveolin-1 cDNA constructed in Example XV.
FIG. 13 represents a photograph showing the results of western blotting for young cells transformed with caveolin-1 cDNA.

Total RNA was isolated from human old fibroblasts using TRIzol (Gibco-BRL, #15596–026) and RT-PCR was then carried out to obtain caveolin-1 cDNA using the isolated RNA. The primers used are: forward primer, 5'-atccaagct-tccaccatgtctgggggcaaatacgt- 3' (SEQ ID NO:9) and reverse primer, 5'-gcaggatccctatatttctttctgcaagttgat- 3' (SEQ ID NO:10). The reverse transcriptase and Taq polymerase used are AMT RTase from Promega and Ex Taq from TaKaRa, respectively. The temperature is set: 60° C. for 30 sec (annealing), 72° C. for 50 sec (extension) and 92° C. for 30 sec (denaturation). The amplified cDNA was verified by DNA sequencing in accordance with chain termination method (Sanger, F. et al., Proc. Natl. Acad. Sci., 74:5463 (1977)). The nucleotide sequence of caveolin-1 cDNA is found in SEQ ID NO:3. The amplified cDNA was subcloned into pcDNA3 (Invitrogen) using restriction sites of HindIII and BamHI. The genetic map of the final constructed vector is shown in FIG. 12.

EXAMPLE XVI

Transformation of Human Fibroblasts with Caveolin-1 cDNA

Young human fibroblasts (PDL 25) were transformed using the vector constructed in Example XV. The cells were plated into the dish and incubated for 18 hrs to allow 70–80% confluency. Two μg of the vector constructed in Example XV was mixed with 8□ of Plus reagent and the resulting mixture was mixed with 12 μl of Lipofectamine (Gibco-BRL) and 238 μl of DMEM, followed by standing the mixture for 15 min. at room temperature. Following the further addition of 2 ml of DMEM, the final mixture was added to young fibroblasts and then incubated for 3 hrs at 37° C. After the lapse of 3 hr., 2.5 ml of DMEM containing 20% FBS were added and incubated for another 24 hr. After 30 hr, the transfected cells were stimulated with 100 μg/ml EGF. Finally, Western blotting was carried out as described in Example V so that the activation of Erk-1/2 may be detected. In FIG. 13, lane 1 of panel A represents sample transformed with pcDNA 3 and lane 2 represents sample transformed with pcDNA 3 carrying caveolin-1 cDNA. As verified in FIG. 13, the cells transformed with pcDNA 3 carrying caveolin-1 cDNA express caveolin-1 protein. In FIG. 13, lanes 1–3 of panel B represent samples transformed with pcDNA 3 and subsequently stimulated with EGF for 0, 5 and 20 min, respectively, and lanes 4–6 of panel B represent samples transformed with pcDNA 3 carrying caveolin-1 cDNA and subsequently stimulated with EGF for 0, 5 and 20 min.

As shown in FIG. 13, the expression of Erk-1/2 kinase was not changed in cells overexpressing caveolin-1 protein whereas the phosphorylation of Erk-1/2 was significantly inhibited in comparison with mock-transformed cells.

These data demonstrate that the activation of Erk- 1/2 kinase is blocked when introducing caveolin-1 DNA into cells and sequentially the responsiveness to stimuli is diminished, thereby leading to cellular senescence. The result reveals that the diminished activation of Erk-1/2 kinase is due to the diminished expression level of caveolin-1 protein.

EXAMPLE XVII

Transfection of Antisense Oligonucleotide to Caveolin-1

XVII-1: Synthesis of Antisense Oligonucleotide to Caveolin-1

To prepare antisense oligonucleotide to inhibit the expression of caveoin-1 protein, a suitable region of caveolin-1 mRNA to interact with antisense oligonucleotide was selected. Thus, the antisense oligonucleotides capable of binding to translational initiation region of caveolin-1 mRNA, which are designed to block translational initiation, were synthesized. The synthesized oligonucleoties were conjugated with fluorescien (Genotech) in their 5'-terminal region and modified by phosphorothioate to increase their stability. For example, the synthesized antisense oligonucleotide has a nucleotide sequence: 5'-tttgcccccaga-3'. The sense oligonucleotide bound to the above region was also synthesized: 5'-atgtctgggggc-3'.

XVII-2: Transfection of Antisense Oligonucleotide to Caveolin-1

Old human fibroblasts (PDL 64) were placed onto 24 well-plate or dish containing DMEM without FBS and incubated in incubator (37° C., 5% $CO_2$) for 12 hr. After incubation, 1–5 μg of 100 μM antisense oligonucleotides synthesized and Plus reagent (Gibco-BRL) were mixed with 500 μM of DMEM and subsequently reacted for 15 min. at room temperature, and the resulting mixture was well mixed with 500 μl of the mixture containing 12 μl of Lipofectamine (Gibco-BRL) and DMEM, followed by standing the mixture for 15 min. at room temperature in order to form liposome complex. The incubated cells were washed twice with DMEM (no serum) and treated with 1 ml of the liposome complex, followed by incubation for 3 hr at 37° C. To the transfected cells, 1–5 ml of DMEM containing 10% FBS was added and the incubation was subsequently carried out for 24 hr, after which the media was changed with DMEM containing 10% FBS. Following incubation for a given period, immunostaining and western blotting were carried out as follows:

XVII-3: Immunostaining

Figure 14:
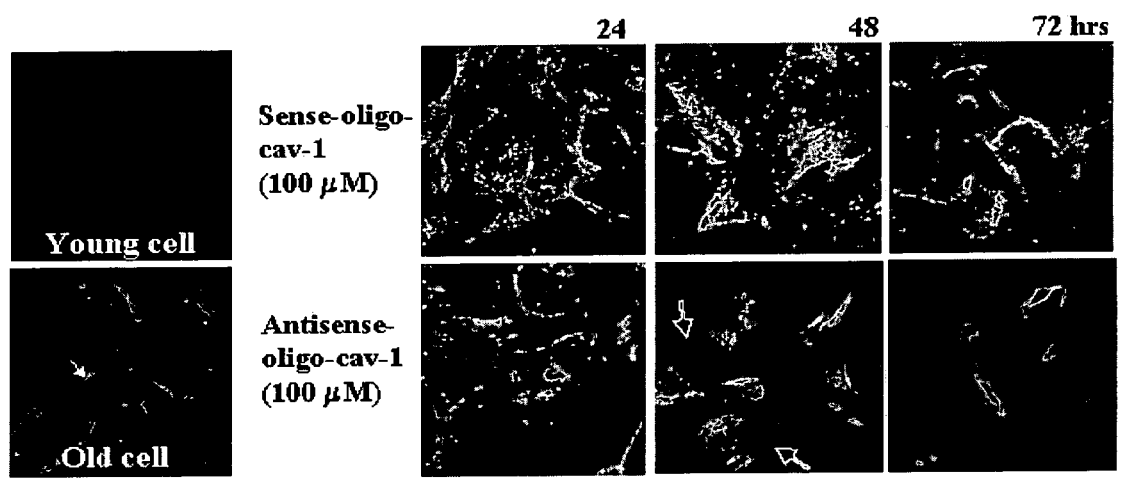
FIG. 14 represents a confocal microphotograph indicating that caveolin-1 expression is dramatically decreased by antisense oligonucleotide.

The cells treated with antisense oligonucleotide were fixed with 0.5 ml of 4% paraformaldehyde for 20 min at room temperature and then permeabilized with 0.5 ml of 0.5% Triton X-100 in PBS for 10 min, followed by blocking with 2% BSA (in PBS). The cells were sequentially incubated with anti-caveolin-1 antibody (Transduction Laboratory) overnight at 4° C. and then rhodamine-conjugated secondary antibody (Santa Cruz) for 1 hr at room temperature. For the purpose of visualizing nucleus, DAPI (Molecular Probe) was also added. The observation was performed using confocal microscope (Biorad, #MRC1024). As shown in FIG. 14, the expression of caveolin-1 in cell is dramatically decreased in the cells treated with antisense oligonucleotide with a lapse of treatment time, while the expression of caveolin-1 is not changed in the cells treated with sense oligonucleotide. Interestingly, the old cells treated with antisense oligonucleotide exhibited the altered cell morphology: enlarged and spread morphology to smaller and spindle morphology. In contrast, the old cells treated with sense oligonucleotide did not show such cell-morphology alteration.

XVII-4: Western Blotting

Western blotting was performed with the cells treated with oligonucleotides in the same manner as Example XII. The cells treated with antisense oligonucleotide provided a weaker band corresponding to caveolin-1, indicating that the expression of caveolin-1 is decreased in the cells treated with antisense oligonucleotide.

Based on the results from immunostaining and western blotting, it is elucidated that caveolin-1 is directly involved in cellular senescence and the inhibition of expression of caveolin-1 leads to not only the prevention of cellular senescence but also the conversion of old cell to young cell.

EXAMPLE XVIII

Analysis of Erk-1/2 Activation Upon Transfection of Antisense Oligonucleotide to Caveolin-1

The old and young fibroblasts were treated with antisense oligonucleotide as described in Example XVII. The EGF stimulation and western blotting were carried out as described in Example XI. FIG. 15 represents the results of this Example. As shown in FIG. 15, Erk-1/2 kinases in young cells were strongly phosphorylated (activated). However, non-treated old cells and treated old cells with sense oligonucleotide showed higher basal Erk-1/2 activity than young cells and when stimulated with EGF, the cells showed no alteration in Erk-1/2 activation. Interestingly, in old cells treated with antisense oligonucleotide, Erk-1/2 activation by EGF was highly increased as young cells.

These observations elucidates that the inhibition of caveolin-1 expression due to the treatment with antisense oligonucleotide, provide old cells with the restoration of signal cascade mediated by Erk, which is typical in young cells.

EXAMPLE XIX

Observation of p-Erk-1/2 Translocation to Nucleus Upon Transfection of Antisense Oligonucleotide to Caveolin-1

To verify that Erk-1/2 kinase activated in Example XVIII is translocated into nucleus and regulate sequentially the expression of other genes, immunostaining was performed as follows: Young and old fibroblasts were treated with antisense oligonucleotide and EGF as Example XIII. The treated cells were sequentially incubated with anti-p-Erk (phosphorylated-Erk) antibody (New England Biotech) overnight at 4° C. and then FITC-conjugated secondary antibody (Santa Cruz) for 1 hr at room temperature. For the purpose of visualizing nucleus, DAPI (Molecular Probe) was also added. The image of p-Erk-1/2 localization was visualized using confocal microscope (Biorad, #MRC1024), which is found in FIGS. 21 and 22. In FIGS. 21 and 22, arrows indicate translocation of p-Erk-1/2 kinase into nucleus.

Figure 16:
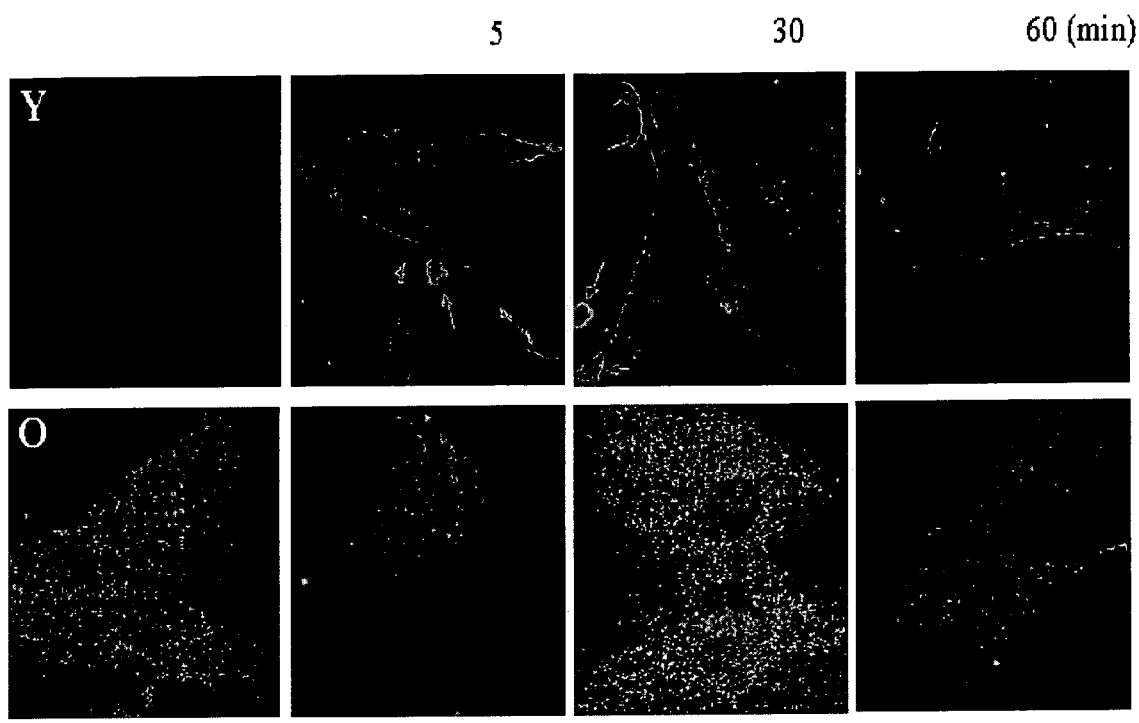
FIG. 16 is a confocal microphotograph representing activation and localization of Erk-1/2 upon epidermal growth factor (EGF) stimulation in young and old cells.

As shown in FIG. 16, in young cells, at 5 min after treatment, p-Erk-1/2 was strongly observed in cytoplasm, at 30 min after treatment, p-Erk-1/2 translocated into nucleus was seen and at 60 min after treatment, p-Erk-1/2 was weakly observed only in cytoplasm. These results indicate that Erk-1/2 is activated (phosphorylated) within 5 min after treatment, the resulted p-Erk-1/2 is translocated into nucleus to regulate transcription of several genes at 30 min and is finally inactivated at 60 min. In contrary to the young cells, old cells exhibited that p-Erk-1/2 was strongly observed in cytoplasm irrespective of EGF treatment, which is also found in the results of western blotting. Interestingly, old cells showed no p-Erk-1/2 translocated into nucleus.

Figure 17:
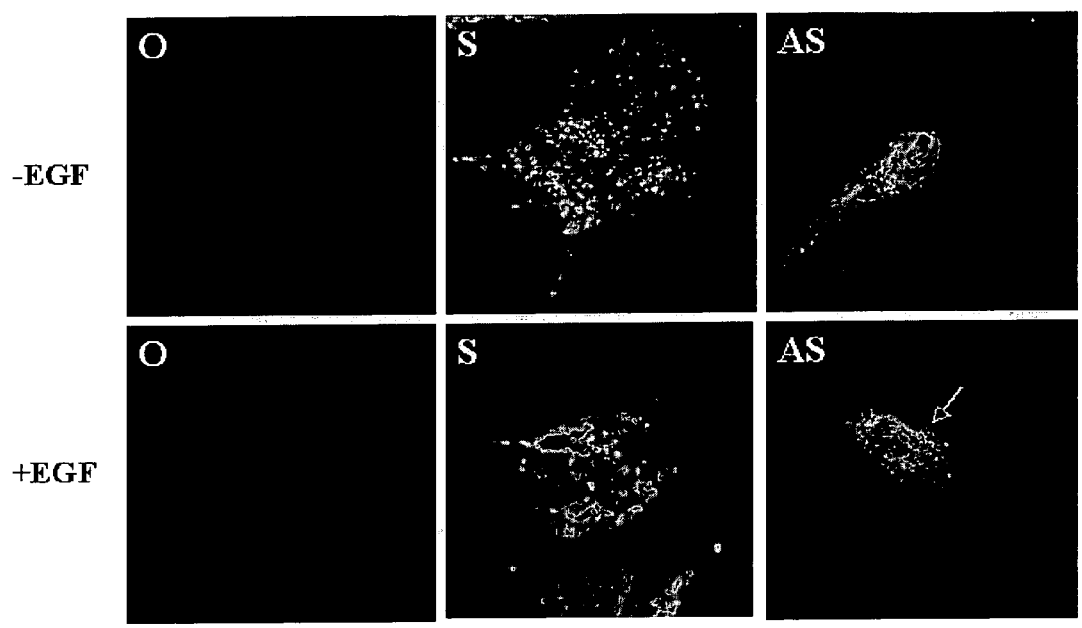
FIG. 17 shows a confocal microphotograph representing activation and localization of Erk-1/2 upon EGF stimulation, in young and old cells, after downregulation of caveolin-1, that is after transfection of antisense oligonucleotide to caveolin-1.

Moreover, as shown in FIG. 17 old cells treated with sense oligonucleotide showed no p-Erk-1/2 in nucleus and vice versa for old cells treated with antisense oligonucleotide.

These results demonstrate that the inhibition of the expression of caveolin-1 with antisense oligonucleotide is responsible for the restoration of Erk-mediated signal cascade. Furthermore, the results indicate that caveolin-1 is also involved in the restoration of translocation into nucleus, which is generally blocked in old cells.

EXAMPLE XX

Methylation of CpG Island of Caveolin-1 Gene

It is well known that upon aging, the expression of p16/Ink4a is increased with the decrease of the methylation level of CpG island located in promoter thereof (Jarrard D.F., *Cancer Res.*, 15;59(12):2957–2964 (1999)). Furthermore, it has been revealed that caveolin-1 also has a similar methylation pattern in cancer cell (Cui *J., Prostate*, 15;46(3): 249–256 (2001)). Therefore, the inventors examined whether the decreased expression of caveolin-1 is ascribed to such methylation.

Young fibroblasts (PDL 20) were treated with 1 µM demethylating agent, 5-aza-deoxycytidine (Sigma) in DMSO and then periodically treated with the agent at the time of changing media for 2–3 weeks. The induction of cellular senescence was verified by SA β-gal activity staining as Example III. To investigate the expression of related proteins, the treated cells were harvested in different days and western blotting was performed as previously described. In western blotting, anti-p53 antibody, anti-p16 antibody, anti-caveolin-1 antibody and anti-actin antibody were purchased from Santa Cruz Biotechnology, Inc.

Figure 18A:
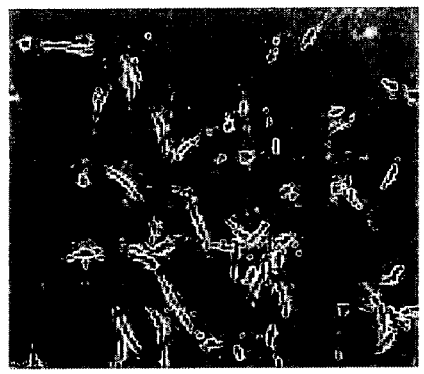
FIG. 18a is a photograph representing the results of senescence-associated β-galactosidase activity staining for young cells treated with demethylating agent, 5-aza-deoxycytidine.
Figure 18A:
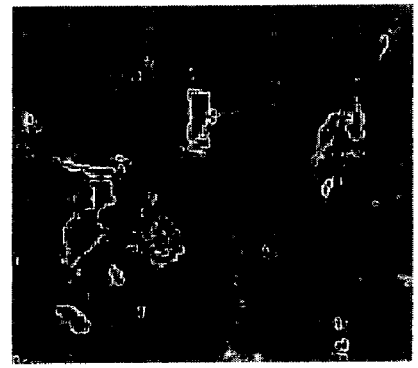
Figure 18B:
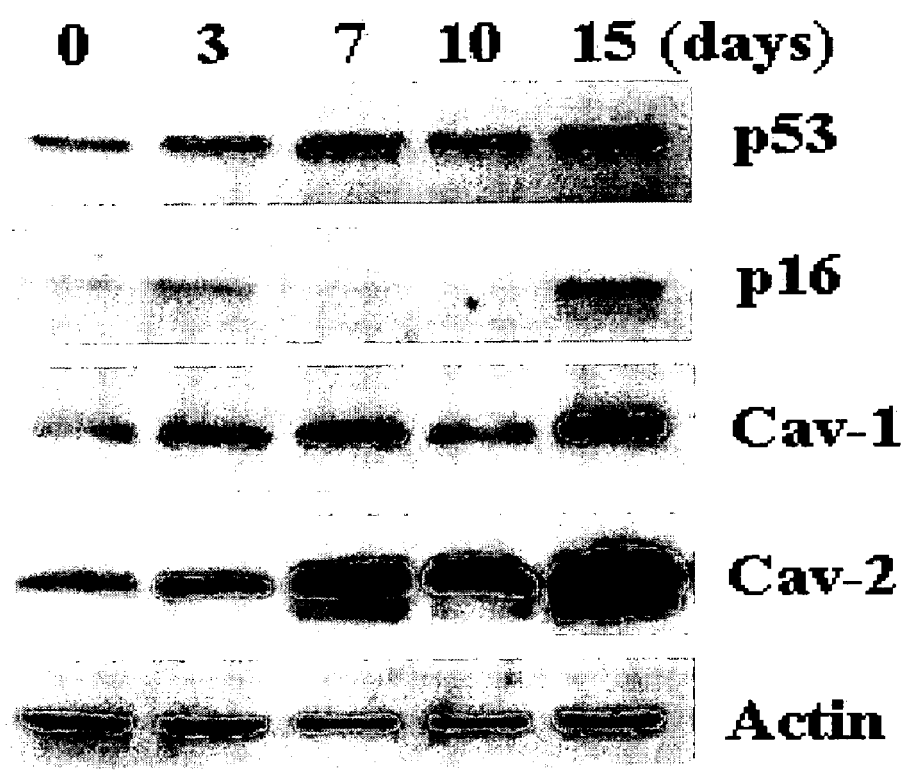
FIG. 18b shows a photograph representing the results of western blotting for young cells treated with demethylating agent, 5-aza-deoxycytidine.

As shown in FIG. 18*a* representing the results of SA β-gal activity staining, the young cells treated for about 2 weeks showed senescent cell-like phenomenon. As shown in FIG. 18*b* representing the results of western blotting, with demethylation, the expression of p16 and caveolin-1 were increased and the expression of p53 was not altered. Interestingly, the increased level of p16 was detected at the early phase of cellular senescence, whereas the increased level of caveolin-1 was detected earlier than p16. These results elucidate that the increased level of caveolin-1 in senescent cells was not leaded directly by either cellular senescence or the increased level of p16 but by demethylation of CpG island in promoter of caveolin-1 gene.

As a result, it is revealed that cellular senescence can be modulated by the methylation level of the promoter, in particular, CpG island of caveolin-1 gene.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for modulating cellular senescence in vitro, comprising introducing into a senescent cell a polynucleotide encoding an amphiphysin-1 protein involved in cellular senescence.

2. The method according to claim 1, wherein the polynucleotide is gDNA or cDNA.

3. The method according to claim 1, wherein the polynucleotide encoding the amphiphysin-1 protein involved in cellular senescence is contained in an expression vector for eucaryotic cells.

* * * * *